(12) United States Patent
Diprose

(10) Patent No.: US 11,083,185 B2
(45) Date of Patent: Aug. 10, 2021

(54) APPARATUS AND METHOD FOR ELECTRICALLY KILLING PLANTS

(71) Applicant: Ubiqutek LTD, Birmingham (GB)

(72) Inventor: Michael Frederik Diprose, Royal Sutton Coldfield (GB)

(73) Assignee: Ubiqutek LTD

( * ) Notice: Subject to any disclaimer, the term of this patent is extended or adjusted under 35 U.S.C. 154(b) by 0 days.

(21) Appl. No.: 16/803,548

(22) Filed: Feb. 27, 2020

(65) Prior Publication Data

US 2020/0245609 A1 Aug. 6, 2020

Related U.S. Application Data

(63) Continuation of application No. 15/329,789, filed as application No. PCT/GB2015/052168 on Jul. 27, 2015, now abandoned.

(30) Foreign Application Priority Data

Jul. 29, 2014 (GB) ...................................... 1413435
Apr. 4, 2015 (GB) ...................................... 1505830

(51) Int. Cl.
*A01M 21/04* (2006.01)
*A01H 3/04* (2006.01)
*A01G 7/04* (2006.01)

(52) U.S. Cl.
CPC ............. *A01M 21/046* (2013.01); *A01H 3/04* (2013.01); *A01M 21/04* (2013.01); *A01M 21/043* (2013.01); *A01G 7/04* (2013.01)

(58) Field of Classification Search
CPC .............................. A01M 21/04; A01M 21/046
USPC .................................................. 47/1.3, 58.1 R
See application file for complete search history.

(56) References Cited

U.S. PATENT DOCUMENTS

| | | |
|---|---|---|
| 2,596,504 A | 5/1952 | Opp |
| 3,935,670 A | 2/1976 | Pluenneke et al. |
| 6,080,362 A | 6/2000 | Wong et al. |
| 6,237,278 B1 | 5/2001 | Persson et al. |
| 2006/0265946 A1 | 11/2006 | Schwager et al. |

FOREIGN PATENT DOCUMENTS

| FR | 2770969 A1 | 5/1999 |
|---|---|---|
| JP | 2003250421 A | 9/2003 |

OTHER PUBLICATIONS

International Search Report, dated Nov. 3, 2015, in PCT/GB2015/052168, filed Jul. 27, 2015.
Written Opinion of the International Searching Authority, dated Nov. 3, 2015, in PCT/GB2015/052168, filed Jul. 27, 2015.

(Continued)

*Primary Examiner* — Christopher D Hutchens
*Assistant Examiner* — Steven J Shur
(74) *Attorney, Agent, or Firm* — Dunlap Codding, P.C.

(57) ABSTRACT

An electrical energy processing unit of an apparatus to kill a plant or at least attenuate plant growth is disclosed. The electrical energy processing unit includes a converter and a control circuit. Also disclosed are an apparatus that includes the electrical energy processing unit and a method of utilizing the apparatus. Further disclosed are a computer program for a processor of the control circuit of the electrical energy processing unit and a non-transitory computer readable medium that includes the computer program.

20 Claims, 9 Drawing Sheets

(56) References Cited

OTHER PUBLICATIONS

U.S. Appl. No. 15/564,082; Michael F. Diprose, filed Oct. 3, 2017; Office Action dated May 16, 2019.
U.S. Appl. No. 15/564,082; Michael F. Diprose, filed Oct. 3, 2017; Amendment and Response to Office Action filed Aug. 16, 2019.
U.S. Appl. No. 15/564,082; Michael F. Diprose, filed Oct. 3, 2017; Final Office Action dated Oct. 29, 2019.
U.S. Appl. No. 15/329,789; Michael F. Diprose, filed May 31, 2017; Office Action dated Apr. 16, 2019.
U.S. Appl. No. 15/329,789; Michael F. Diprose, filed May 31, 2017; Amendment and Response to Office Action filed Aug. 5, 2019.
U.S. Appl. No. 15/329,789; Michael F. Diprose, filed May 31, 2017; Final Office Action dated Oct. 29, 2019.
Elliott, Valerie; "Weedinator! The New Pesticide-Free Way to Clear your Garden. But Beware . . . It Packs as Many Volts as the Electric Chair,"; Daily Mail.com (Jan. 21, 2012); https://www.dailymail.co.uk/news/article-2090021/Weedinator-The-new-pesticide-free-way-clear-garden-But-beware--packs-volts-electric-chair.html; 4 pages.
Bell, Carl; "Electrocuting Weeds," UC Weed Science—ANR Blogs (Feb. 26, 2014); 3 pages.
"Lightning Weeder: Kills Weeds With Electricity," Farm Show Magazine (1981) 5(2):21.
EP Appl. No. 15747183.0; Ubiqutek Ltd. filed Jul. 27, 2015; Office Action dated Apr. 17, 2018.
EP Appl. No. 15747183.0; Ubiqutek Ltd. filed Jul. 27, 2015; Response to Office Action dated Jun. 29, 2018.
EP Appl. No. 15747183.0; Ubiqutek Ltd. filed Jul. 27, 2015; Office Action dated Oct. 31, 2018.
EP Appl. No. 15747183.0; Ubiqutek Ltd. filed Jul. 27, 2015; Response to Office Action dated Nov. 29, 2018.
EP Appl. No. 15747183.0; Ubiqutek Ltd. filed Jul. 27, 2015; Intent to Grant dated Mar. 28, 2019.
EP Appl. No. 15747183.0; Ubiqutek Ltd. filed Jul. 27, 2015; Office Action dated Mar. 17, 2017.
EP Appl. No. 15747183.0; Ubiqutek Ltd. filed Jul. 27, 2015; Response to Office Action dated Sep. 27, 2017.
EP Appl. No. 15747183.0; Ubiqutek Ltd. filed Jul. 27, 2015; Decision to Grant an European Application dated Aug. 22, 2019.

3kV

| Frequency (kHz) | 5 | 10 | 15 | 20 | 25 | 30 | 35 | 40 | 45 | 50 |
|---|---|---|---|---|---|---|---|---|---|---|
| Kill Effectiveness (%) | 25 | 35 | 20 | 100 | | 50 | | 20 | | |

4kV

| Frequency (kHz) | 5 | 10 | 15 | 20 | 25 | 30 | 35 | 40 | 45 | 50 |
|---|---|---|---|---|---|---|---|---|---|---|
| Kill Effectiveness (%) | 80 | 90 | 100 | 100 | 80 | 100 | 40 | 80 | 60 | |

5kV

| Frequency (kHz) | 5 | 10 | 15 | 20 | 25 | 30 | 35 | 40 | 45 | 50 |
|---|---|---|---|---|---|---|---|---|---|---|
| Kill Effectiveness (%) | 100 | 100 | 100 | 83 | 100 | 100 | 100 | 60 | 100 | 100 |

6kV

| Frequency (kHz) | 5 | 10 | 15 | 20 | 25 | 30 | 35 | 40 | 45 | 50 |
|---|---|---|---|---|---|---|---|---|---|---|
| Kill Effectiveness (%) | 100 | 100 | 100 | 100 | 100 | 100 | 100 | 100 | 100 | 100 |

APPARATUS AND METHOD FOR ELECTRICALLY KILLING PLANTS

CROSS REFERENCE TO RELATED APPLICATIONS/INCORPORATION BY REFERENCE STATEMENT

This application is a continuation of U.S. Ser. No. 15/329,789, filed Jan. 27, 2017; which is a US national stage application filed under 35 USC § 371 of International Application No. PCT/GB2015/052168, filed Jul. 27, 2015; which claims priority to Application NO. GB 1413435.7, filed Jul. 29, 2014; and Application No. GB 1505830.8, filed Apr. 4, 2015. The entire contents of the above-referenced patent applications are hereby expressly incorporated herein by reference.

TECHNICAL FIELD

The present invention relates to electric apparatus that is configured to attenuate plant growth by the application of electrical energy thereto.

BACKGROUND

In properties both commercial and domestic it is common to kill or at least control the growth of unwanted plants, commonly referred to as weeds. A conventional process for doing so is to extract manually or by means of a mechanical implement, the weed from the ground. It is preferable to extract the weed in its entirety with its roots intact, as a portion that remains in the ground can re-grow. A drawback with such a process is that ensuring entire extraction is laborious and particularly difficult. A further drawback is that weeds can seed or re-grow quickly, particularly in warm and wet climates, which means that regular repetitions of the process are required. A yet further drawback is that mechanically removing a weed can disturb the surrounding soil such that: buried seeds are surfaced; crops/seeds are inadvertently removed via the interconnecting soil of the weed that is removed with the weed; the soil is subject to nutrient and moisture loss.

A solution to the above drawbacks is the process of chemically poisoning the weed by means of a pesticide or more particularly a herbicide. Desirably, herbicides can be formulated to selectively target specific weeds whilst leaving a desired crop relatively unharmed. Such herbicides may function by interfering with the growth of the weed and are often synthetic mimics of natural plant hormones. Exposure of herbicides to humans and animals can arise as a result of improper application, for example, contact during application or as a residue on foodstuffs or other contamination of the food chain. Such exposure is undesirable since a known drawback with herbicides is that they can be toxic to humans and animals. More particularly, herbicides can cause various health problems such as skin and respiratory conditions. There are also concerns over carcinogenicity (e.g. Triazine and Phenoxy herbicides) as well as a relationship with Parkinson's disease. A further drawback is that herbicides are not always successful in killing the target weeds. A yet further drawback is that herbicides can be washed off plants if rain follows their application or blown away due to wind thereby restricting the times of application. A yet further drawback is that herbicides can be harmful to the surrounding environment, for example, they can be transported via leaching or surface runoff to contaminate groundwater or distant surface water sources. Transport of herbicides is promoted by intense rainfall and soils with limited absorption and retention. These effects are confounded if the particular herbicide has high persistence (resistance to degradation) and water solubility. As a result of these numerous drawbacks there are increasingly severe restrictions on the use of herbicides, particularly throughout the European Union. Moreover, as a result of these numerous drawbacks consumers are increasingly demanding organic produce, for which the use of herbicides is prohibited.

A solution to the above drawbacks is the process of killing the weed by means of the application of electrical energy thereto. Apparatus used in such a process generally comprise: an electrical energy source that is arranged with a high-voltage side in electrical contact with applicator electrodes; the applicator electrodes configured to transfer the high-voltage to the weed; a low-voltage side of the electrical energy source connected to ground thus completing a circuit whereby the load comprises a current drawn through the weed. Advantageously, such a process does not contaminate the environment to the same extent as a herbicidal process nor is it as toxic to humans and animals.

U.S. Pat. No. 4,338,743 discloses such apparatus, wherein the electrical energy source comprises an engine-generator and a high-voltage transformer. The generator supplies electrical current to a primary winding of the high-voltage transformer, the high-voltage transformer has a secondary winding electrically connected to applicator electrodes. The applicator electrodes are configured for direct transmission of the high-voltage to weeds. The apparatus is for agricultural use and is disposed on a vehicle that can be towed by an agricultural vehicle. The apparatus functions in a first mode: wherein the high-voltage is applied to the applicator electrodes or in a stand-by mode: wherein electrical energy is supplied from the generator to electrical outlets that can be used to supply other agricultural equipment. The apparatus is operable to generate 14.4 kV at 60±5 Hz at the applicator electrodes. A drawback with this apparatus is that the high-voltage transformer is bulky. A further drawback is that the output at the applicator electrodes is particularly dangerous to humans and animals.

U.S. Pat. No. 5,600,918 discloses further such apparatus, wherein the electrical energy source comprises a piezoelectric crystal and an actuator. The actuator is configured to apply a compressive force to the piezoelectric crystal to thereby generate a high-voltage that is electrically connected to the applicator electrodes. The apparatus is operable to generate 50-1500 V in short bursts at the applicator electrodes. Advantageously, the apparatus does not require a bulky transformer, however it is limited to non-agricultural applications due to the particularly limited power the piezoelectric crystal can supply.

A solution to some of the drawbacks of the above apparatus is provided in JP 2002360151, which discloses a yet further such apparatus, wherein the electrical energy source comprises a battery that supplies a direct current of 24 V to an oscillating unit and a high-voltage transformer. The oscillating unit outputs an oscillating signal to transistors that switch with the oscillating signal to effect the switching of a current through a primary coil of the high-voltage transformer. The high-voltage transformer is configured such that the voltage over a secondary coil is stepped-up to 6 kV with a frequency of 15 kHz and a low current of 0.5 mA. The secondary coil is electrically connected to an electrode that comprises a dielectric outer layer. The apparatus is configured to cause corona discharge at the leaves of the weed and yield ozone that acts to chemically poison the weed. Due to the particular low current the body of the weed is generally not targeted. Accordingly, the apparatus is in general limited to the treatment of small areas and is therefore not suitable for agricultural use.

A further solution to some of the drawbacks of the above apparatus is provided in JP H3-83534, and the related publication: 'Destruction of Weeds by Pulsed High-Voltage Discharges', A. Mizuno, T. Tenma and N. Yamano, Toyohashi University of Technology, 1990, wherein the electrical energy source comprises a DC electrical source and a capacitor. The capacitor is sequentially: connected to the DC electrical source and charged; disconnected from the DC electrical source; connected to an applicator electrode and discharged therefrom as a spark. The applicator electrode transmits the generated spark through the air to the nearest weed, i.e. without direct contact between the weed and electrode. Accordingly the apparatus is not configured for direct contact between the applicator electrode and the weed. The spark comprises 15 kV at 30 pulses per second. A drawback with this apparatus is that the path of the spark is potentially unpredictable due to arcing and therefore could be transmitted to nearby humans and animals. A further drawback is that since the voltage is particularly high there is a significant risk of injury from high current transfer. A yet further drawback is that there is a risk of fire due to ignition of the weed/surrounding plants. A yet further drawback is that the use of a capacitor in this way generally limits the apparatus to the treatment of small areas and small weeds: the apparatus it is therefore not particularly suitable for agricultural use.

A yet further solution to some of the above drawbacks of the above apparatus is provided in the publication: 'A Portable Weed Control Device using High Frequency AC Voltage', A. Mizuno, A. Nagura, T. Miyamoto and A. Chakrabarti, Toyohashi University of Technology, 2001, wherein an electrical energy source comprises a DC electrical source that supplies a direct current of 12V to an oscillating circuit and a high-voltage transformer. The oscillating circuit outputs an oscillating signal to effect the switching of a current through a primary coil of the high-voltage transformer. The high-voltage transformer is configured such that the voltage over a secondary coil is stepped-up to 3 kV with a frequency of 12.5 kHz. The secondary coil is electrically connected to an applicator electrode, which is in electrical contact with a weed. A drawback with this apparatus is that high-voltage output at the applicator electrodes is still particularly dangerous to humans and animals. A further drawback is that the apparatus is in general limited to the treatment of small areas and is therefore not suitable for agricultural use.

BRIEF DESCRIPTION OF THE DRAWINGS

For a better understanding of the invention, and to show how embodiments of the same may be carried into effect, reference will now be made by way of example to the accompanying diagrammatic drawings in which.

DETAILED DESCRIPTION

Figure 1:
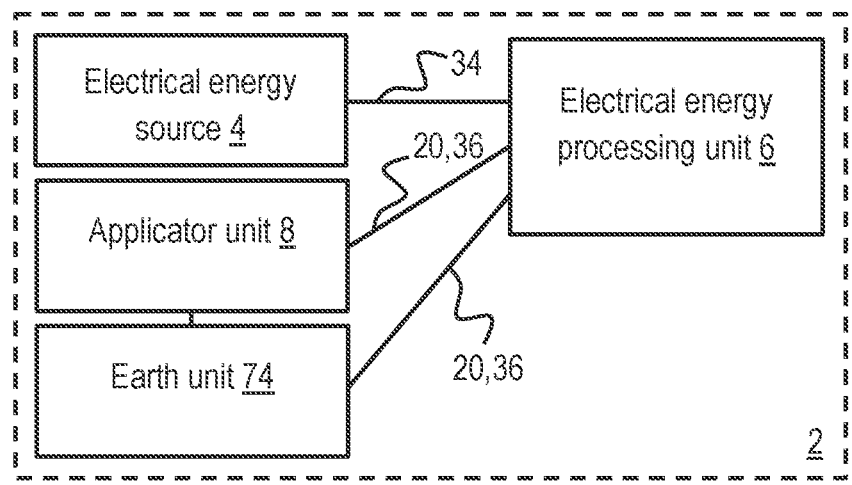
FIG. 1 is a block diagram of electrical weed killing apparatus according to the invention.

An object of the invention is to provide apparatus to electrically control plant growth that is effective such that it may replace herbicides and/or physical extraction in a range of environments, i.e.: agricultural; commercial (e.g. on sports fields, golf courses); private non-commercial (home use).

An object of the invention is to provide apparatus to electrically control plant growth that is relatively safe to use.

It would be advantageous to provide apparatus to electrically control plant growth that is cost-effective to manufacture.

It would be advantageous to provide apparatus to electrically control plant growth that is compact.

It would be advantageous to provide apparatus to electrically control plant growth that is convenient to use.

It would be advantageous to provide apparatus to electrically control plant growth that can quickly control plant growth.

Objects of the invention are achieved by: the electrical energy processing unit according to claim 1; the apparatus according to claim 9; the method according to claim 14; the use according to claim 16; the computer program according to claim 17.

Disclosed herein and according to a first aspect of the invention is an electrical energy processing unit of apparatus to electrically control plant growth, the electrical energy processing unit comprising: a converter configured to receive unprocessed electrical energy from an electrical energy source, to convert the unprocessed electrical energy to processed electrical energy and to output said processed electrical energy to an applicator unit. Typically the converter is configured to transmit the said processed electrical energy between an applicator electrode of an applicator unit and an earth electrode of an earth unit. More particularly converter may be configured to transmit the processed electrical energy through a processed electrical energy circuit. The processed electrical energy circuit may comprise: an applicator electrode of an applicator unit; an earth electrode of an earth unit; in use a treated plant and the ground. The electrical energy processing unit may comprise a control circuit operable to control the converter to convert the unprocessed electrical energy to the processed electrical energy. In an example wherein the converter provides a fixed operation on the unprocessed electrical energy it will be appreciated that a control circuit is not required. However, generally the electrical energy processing unit comprises a control circuit when control of the said converter is required, e.g. to provide a varying output of an aspect, (e.g. voltage, current or power) of the processed electrical energy. The processed electrical energy is suitable for killing a plant or at least partially attenuating plant growth. The processed electrical energy comprises a waveform, which can have a repeating unit various shapes, with a frequency of at least 18 kHz. The processed electrical energy may have a peak voltage of above 1 kV or more particularly within one of the following ranges: 1 kV to 30 kV; 2 kV to 20 kV; 2.5 kV to 17.5 kV. The peak voltage is defined as the peak amplitude of the repeating units of the waveform. The frequency is defined as the number of repeating units of the waveform per unit time. A repeating unit is defined as a unit that repeats with substantially the same form, e.g. it may comprise waveforms of substantial the same shape including when the amplitude and/or duty cycle or period is adjusted for control of the processed electrical energy.

Advantageously, objects of the invention are solved since processed electrical energy that comprises a waveform with a frequency of at least 18 kHz or more particularly of at least: 20 or 25 or 30 or 35 or 40 or 50 kHz is less of a safety risk to humans and animals than the apparatus of the prior art, which operate outside this frequency range. In more detail, it has been found that for electrical current above such frequencies the nerve and muscle tissue systems of humans and animals do not have time to react to the current. In more detail, the said nerve systems have transport mechanisms that comprise chemical ion transmission across a cell membrane. Said transport mechanisms occur over a finite amount of time, referred to as a chronaxia, e.g. the chronaxia of a nerve cell may be 0.1-10 ms. For electrical frequencies in the said range it has been found that the electrical shock ceases to become apparent and the nerve system may not respond in a substantially detrimental manner.

Moreover, objects of the invention are solved since a processed electrical energy that comprises a waveform with a frequency of at least 18 kHz or more particularly of at least: 20 or 25 or 30 or 35 or 40 or 50 kHz is believed to be effective at controlling plant growth than the apparatus of the prior art, which operate outside this frequency range. In particular it is believed that plants tend to conduct the said high-frequency current through their outer layers, with damage being by heat to the said conducting layers. In a stem of a plant the outer layers comprise: xylem; phloem; sclerenchyma; cortex; epidermis, whereas the inner layers comprise the protoxylem and pith. It is believed that the high-frequency current is in particular concentrated in the xylem and/or phloem that comprise the living tissue of the plant for the transportation of water and other nutrients. Accordingly, they are critical to the plant and are more specifically targeted by the current in the claimed high-frequency range.

The electrical energy processing unit is configured to produce processed electrical energy to kill a plant (e.g. immediate destruction of the plant such that the plant does not grow back) or at least attenuate the growth of a plant (e.g. such that the natural growth of a plant is substantially reduced). The electrical energy processing unit is configured to produce processed electrical energy that has an initial current of at least 10 mA or 50 mA or 100 mA or 500 mA (rms or peak). The current is sufficient for substantial damage of the body, i.e. the stem of the plant as it travels therethrough. The electrical energy processing unit is configured to produce processed electrical energy that has a power (i.e. the initial power when first applying the electrical energy to a plant) of at least 5 W or 10 W or 50 W or 100 W. The electrical energy processing unit is configured to produce processed electrical energy that is operable to kill a plant or at least partially attenuating plant growth with a treatment time of at least 10 or 100 milliseconds. The maximum frequency may be 5 MHz or 2 MHz or 1 MHz or 500 kHz or 350 kHz or 100 kHz or 75 kHz or 50 kHz or 40 kHz or any value therebetween.

The abovementioned minimum and maximum frequency ranges may be combined in any manner (i.e. such that the maximum frequency is greater than the minimum frequency). The preferred frequency range may for example be selected as 18 kHz-500 kHz or 20 kHz-100 kHz or 30 kHz-50 kHz. It will be appreciated that as the frequency is increased, i.e. from 18 kHz, the abovementioned effects increase.

Advantageously, by configuring the electrical energy processing unit to operate at the said high-frequency range it can be made particularly compact since suitable high-frequency components are generally more compact than those that are configured to operate at a low-frequency.

The processed electrical energy may comprise a periodic or aperiodic waveform, i.e. a waveform that continuously repeats with the repeating units therein having a constant or a varying period, e.g. a pulsed wave with a fixed duty cycle or a varying duty cycle. The shape of the repeating unit may be one of or a combination of one or more of the following forms: sine wave; saw-tooth wave; triangular wave; square wave; pulsed, e.g. DC pulsatile, half-wave rectified; other known form. The exact shape of the repeating unit may be an approximation of one of the aforesaid forms for reasons of distortion, e.g. overshoot/undershoot and the associated ringing and settle time. The repeating unit may be positive or negative or a combination thereof with respect to a reference value, which is typically 0 V.

The control circuit generally controls the converter by means of a control signal. The form of the processed electrical energy may generally correspond to that defined by the control signal (e.g. an AC or DC waveform) but may be an approximation thereof for reasons of distortion.

The control aspect of the control circuit may be a simple function, e.g. on/off of the processed electrical energy e.g. for an electrical energy processing unit configured to produced processed electrical energy of a fixed waveform. In a more sophisticated example the control aspect may be the control of one or more of a list comprising the following aspects of the waveform of the processed electrical energy: form; duty cycle, which is typically in the range of 0.05-0.45 (e.g. for a pulsed waveform); on/off; amplitude (e.g. to maintain the peak voltage at a particular magnitude for varying load); frequency; period; current; power; shape; other aspect.

The control circuit is preferably configured to control the aspect of the processed electrical energy, which is generally one or more of the: voltage; current; power. The control circuit may be configured to control the aspect to be: maintained substantially at a predetermined value; and/or below or above a predetermined value (e.g. a different to the substantially maintained predetermined value); and/or within a particular range, which is determined by a first and second predetermined value (e.g. the first and second predetermined values are different to each other, and may be different to the aforesaid predetermined values). The control is generally for the said aspect of the processed electrical energy through or over a load as the load varies during treatment, whereby the load comprises a current drawn through a treated plant.

Substantially at a predetermined value may be defined as being ±1 or 2.5 or 5% of a particular value of the aspect. In the configuration wherein the aspect is voltage the particular value may for example be 5 or 10 kV (e.g. the peak or rms voltage). In the configuration wherein the aspect is current the particular value may for example be 0.1 or 0.5 A (e.g. the peak or rms current). In the configuration wherein the aspect is power the predetermined value may for example be 500 or 1000 W.

Below or above a predetermined value can simply delimit the maximum or minimum value of the aspect. In the configuration wherein the aspect is voltage the predetermined value may for example be 5 or 10 kV (e.g. the peak or rms voltage), such that this value is either not exceeded or set as the minimum. In the configuration wherein the aspect is current the particular value may for example be 0.1 or 0.5 A (e.g. the peak or rms current), such that this value is either not exceeded or set as the minimum. In the configuration wherein the aspect is power the predetermined value may for example be 500 or 1000 W such that this value is either not exceeded or set as the minimum. The maximum or minimum value may alternatively be defined as ±5 or 15 or 20 or 25% of a nominal value, e.g. the aforesaid voltage, current or power values.

Within a particular range defined by a first and second predetermined value simply delimit the maximum and minimum value of the aspect. In the configuration wherein the aspect is voltage the first predetermined value may for example be 5 kV and the second predetermined value may for example be 10 kV (e.g. the peak or rms voltage), such that the voltage is maintained at above 5 kV and below 10 kV. In a similar fashion example values of 0.1 or 0.5 A (e.g. the peak or rms current) and 500 or 1000 W can be used for current and power. The first and second predetermined value may alternatively be defined as ±5 or 15 or 20 or 25% of a nominal value, e.g. the aforesaid voltage, current or power values.

The control circuit may be configured to control one or more of the aforesaid aspects by controlling an amplitude and/or duty cycle or period of the processed electrical energy. Such control may be open loop or closed loop control using the converter feedback signal.

In the configuration wherein the said aspect is the voltage, the control circuit may be configured to: in response to a decreasing voltage (e.g. the peak or rms voltage) of the processed electrical energy increase the amplitude and/or duty cycle or period thereof; and/or in response to an increasing voltage of the processed electrical energy decrease the amplitude and/or duty cycle or period thereof. In the configuration wherein the said aspect is the current or power, the control circuit may be configured to: in response to a decreasing current (e.g. the peak or rms current) of the processed electrical energy increase the amplitude and/or duty cycle or period thereof; and/or in response to an increasing current of the processed electrical energy decrease the amplitude and/or duty cycle or period thereof.

The control circuit may be configured allow the said aspect to initially increase from a first value to a second value, wherein when achieving the second value the said aspect is controlled in the one of the aforesaid manners. As an example of this configuration of control: in the configuration wherein the aspect is voltage the first value may for example be 2 kV and the second value may be 5 kV, wherein when 5 kV is achieved the control is implemented, e.g. to: maintain the voltage substantially at 5 kV or be ±20% of 5 kV or if the voltage decreases from 5 kV the duty cycle or period and/or amplitude of the processed electrical energy is increased.

The converter may comprise at least one sensor, the control circuit being operatively connected to the sensor to receive therefrom a converter feedback signal, the converter feedback signal comprising information to monitor the processed electrical energy. The sensor(s) of the converter may be a voltage sensor and/or a current sensor and the corresponding converter feedback signal may comprise voltage and/or current information.

The control circuit may be configured to provide open-loop control of the said one or more aspects of the output processed electrical energy. Alternatively, the control circuit may be configured to provide closed-loop control of the said one or more aspects of the processed electrical energy using the said converter feedback signal. The said control of the processed electrical energy is typically via control of the waveform signal e.g. via a control of the waveform generation unit and other associated units when present.

The control circuit may further be operable to control operation of one or more of the; applicator unit; earth unit; electrical energy source, e.g. by an electrical energy source feedback and control signal.

Typically the control circuit comprises a processor, e.g. to output the said control signal to control the converter. The processor generally provides the aforesaid control of the processed electrical energy. The control circuit may further comprise a user interface operably connected to the processor for control of the operation of the processor and/or for monitoring of the operation of one of more of a list comprising the following: electrical energy processing unit; applicator unit; earth unit; electrical energy source. Alternatively, there is no user interface, e.g. the control circuit is operated automatically in response to an applied current from the electrical energy source.

The converter is configured to convert the unprocessed electrical energy to the desired form of processed electrical energy e.g. via conversion one or more of the: voltage; current; frequency; other optional aspects of the waveform.

The converter may comprise a converter unit which may have various configurations depending on its mode of operation, e.g.: the converter converts only frequency (e.g. the unprocessed electrical energy is supplied at the desired voltage) and the converter unit comprises an electrically operated chopper switch, the switch arranged in series with the unprocessed electrical energy; the converter converts only voltage (e.g. the unprocessed electrical energy is supplied at the desired frequency) and the converter unit comprises a variable or non-variable transformer. In further examples the converter unit may comprise a charge pump or boost converter or other suitable electrical component.

Generally energy the converter increases the voltage and applies the desired frequency, e.g. the unprocessed electrical energy is of a lower voltage than the processed electrical energy and has a direct current. In such an example the control circuit of the electrical energy processing unit may comprise a waveform generation unit and a processor. The waveform generation unit is configured to generate a control signal comprising a waveform signal, e.g. the processor is configured to control the converter via the waveform generation unit (and other associated components when present). The waveform signal generally comprises a non-steady AC or DC signal that is representative of the waveform of the processed electrical energy, e.g. is it amplified by the converter to derive the required form of the processed electrical energy. The waveform of the waveform signal may be controlled by the processor in terms of its: form; duty cycle, which is typically in the range of 0.05-0.45 (e.g. for a pulsed waveform); on/off; amplitude (e.g. to maintain the peak voltage at a particular magnitude for varying load); frequency; period; current; power; shape; other aspect, e.g. to control the processed electrical energy in one of the aforesaid manners. The processor and waveform generator may be an integrated unit, e.g. an integrated circuit or separate units in communication via a control signal. Generally the waveform generation unit is part of the aforesaid control circuit that comprises the processor. However, waveform generation unit may comprise an electronic component operable to generate a fixed waveform output, e.g. with no input other than an electrical energy supply. For example it may comprise any suitable signal generator that may be arranged as an integrated circuit. In such an example the processor may be obviated. In such an example the converter may comprise a switching unit and a converter unit. The switching unit may comprise one or more electrically operated switch, the said switch to receive the control signal and to switch therewith the unprocessed electrical energy. The electrically operated switch can be a transistor or a triac or other suitable component. In such an example the converter unit may comprise a transformer. The transformer may be arranged with the switched unprocessed electrical energy through a primary winding thereof and the processed electrical through a secondary winding thereof. In such an example the converter unit may comprise another suitable electrical component such as a charge pump or boost converter.

Disclosed herein according to a second aspect of the invention is apparatus to electrically control plant growth comprising the electrical energy processing unit according to any feature of the first aspect and at least one applicator unit to apply the processed electrical energy to a plant. The applicator unit may comprise an applicator electrode. The applicator electrode may comprise an electrically conductive material (e.g. a material with high electrical conductivity, such as a metal and not a dielectric material), which is connected to the converter of the electrical energy processing unit to receive therefrom the processed electrical energy. The applicator electrode is preferably configured for direct transmission of the processed electrical energy to a plant, e.g. a substantial portion of the applicator electrode is exposed so that it can touch a plant for the direct transmission of the processed electrical energy thereto. The applicator electrode may alternatively be configured for transmission of the processed electrical energy to the plant by arcing, i.e. spark transmission, without directly touching the plant (e.g. it has associated therewith an insulating housing to prevent direct contacting between the electrode and plant).

The applicator electrode of the applicator unit may further comprise a dielectric material, which is arranged with the processed electrical energy transmitted through (e.g. substantially or fully through) the said dielectric material to a treated plant (e.g. transmission is in the order of: electrically conductive material; dielectric material; plant). The dielectric material is preferably operable to conduct the processed electrical energy by capacitive action. The dielectric material may comprise a layer or coating on the electrically conductive material, e.g. on an exposed outer surface thereof. The dielectric material may have a thickness of at least 0.1 or 0.5 or 1 mm. The dielectric material may have a maximum thickness less than or equal to 2 or 5 or 10 mm.

The apparatus to electrically control plant growth may further comprise an earth unit comprising an earth electrode. The earth electrode may comprise an electrically conductive material (e.g. a material with high electrical conductivity, such as a metal and not a dielectric material), which is connected to the converter to receive the processed electrical energy transmitted from the applicator unit through a load comprising a plant. The earth unit completes a current path comprising the: electrical energy source; electrical energy processing unit; applicator unit; treated plant; ground; earth unit; electrical energy processing unit; electrical energy source. The earth electrode may be configured to receive the high voltage electrical energy when inserted into the ground. Alternatively, the earth electrode may be configured to receive the high voltage electrical energy when resting on a surface of the ground, i.e. to maintain electrical continuity between the ground and the earth electrode when resting on the surface of ground, e.g. such that the processed electrical energy transmitted from the applicator unit to a plant and into the ground can be transmitted from the ground to the earth unit without the earth unit needing to be inserted into the ground. Preferably, the earth electrode is configured to maintain electrical continuity with the ground whilst being moved along the ground, e.g. by sliding or rolling as part of a rotary member. Typically an earth electrode of this type is configured to have a substantially flat surface to abut the ground, e.g. with a surface area of at least 5 or 10 or 20 or 50 $cm^2$, e.g. as a plate. Typically an earth unit of this type is for use when the frequency of the processed electrical energy is above 20 or 25 or 40 or 50 or 75 or 100 kHz.

The earth electrode of the earth unit may further comprise a dielectric material, which is arranged with the processed electrical energy being transmitted through (e.g. substantially or fully through) the said dielectric material to the electrically conductive material (e.g. transmission is in the order of: plant; dielectric material; electrically conductive material). The dielectric material is preferably operable to conduct the processed electrical energy by capacitive action. The dielectric material may comprise a layer or coating on the electrically conductive material, e.g. on an exposed outer surface thereof. The dielectric material may have a thickness of at least 0.1 or 0.5 or 1 mm. The dielectric material may have a maximum thickness less than or equal to 2 or 5 or 10 mm.

The apparatus to electrically control plant growth may comprise an electrical energy source connected to the electrical energy processing unit and/or means for connecting an electrical energy source to the electrical energy processing unit (e.g. a plug). The electrical energy source may comprise one of the electrical energy sources selected from the following: engine-generator; battery; fuel cell; mains electrical supply; vehicle power take-off shaft driving a generator. The electrical energy source (as in the aforementioned examples) may be a portable (e.g. the battery) or external source (e.g. an AC line supply). The means for connecting may comprise part of an electrical interface, e.g. a plug.

Disclosed herein according to a third aspect of the invention is a method of electrically controlling plant growth comprising: supplying processed electrical energy to a plant using the apparatus to electrically control plant growth according to any feature of the second aspect, wherein the processed electrical energy comprises a waveform, which can have a repeating unit various shapes, with a frequency of at least 18 kHz and with a peak voltage of at least 1 kV or other said frequency and voltage range.

The method may further comprise controlling an aspect of the processed electrical energy. The said aspect may be controlled by controlling an amplitude and/or duty cycle or period of the processed electrical energy. The said aspect may be one or more of the: voltage; current; power. The control may be open loop or closed loop using the converter feedback signal. The method may further comprise controlling the said aspect to be: maintained substantially at a predetermined value; or below or above a predetermined value; or within a particular range, which is determined by a first predetermined value and second different predetermined value.

The method may comprise using the apparatus to electrically control plant growth that comprises the earth unit comprising the aforesaid earth electrode that is configured to receive the high voltage electrical energy when resting on a surface of the ground (e.g. arranged planar to the ground, e.g. without insertion into the ground) to: electrically control the growth of a first plant located at a first location and a second plant located at a second location by: moving the earth electrode of the earth unit along the ground whilst maintaining electrical continuity between the earth unit and the ground, e.g. electrical continuity is maintained without the need to insert the electrode of the earth unit into the ground. The applicator unit can be moved between operational proximity of the first location and operational proximity of the second location whilst moving the earth electrode of the earth unit resting substantially on the ground between operational proximity of the first location and operational proximity of the second location.

The method may comprise establishing a threshold voltage. The method may comprise determining a treatment time. The threshold voltage and treatment time may be determined from experimental data, (e.g. a database) and/or predicted (e.g. based on relevant experimental data).

Disclosed herein according to a fourth aspect of the invention is the use of an electrical energy processing unit according to any feature of the first aspect for treating a plant to kill or at least attenuate growth thereof.

Disclosed herein according to a fifth aspect of the invention is a computer program for a processor of a control circuit of apparatus to electrically control plant growth according to any feature of the second aspect, the computer program comprising program code to control (e.g. when executed) the converter (e.g. via a waveform generation unit or via direct control thereof) to generate processed electrical energy with a waveform that has a frequency of at least 18 kHz and with a peak voltage of at least 1 kV. The program code may be for programing of the processor, e.g. for upload onto a memory unit thereof or for programing of programmable logic of the processor.

The computer program may further comprise program code to: control an aspect of the processed electrical energy. The said aspect may be controlled by controlling an amplitude and/or duty cycle or period of the processed electrical energy. The said aspect may be one or more of the: voltage; current; power. The control may be open loop or closed loop using an input converter feedback signal. The computer program may further comprise program code to: control the said aspect to be maintained substantially at and/or below and/or above a predetermined value and/or within a particular range, the range being determined by a first and second predetermined value. Other features controlled by the program code of the computer program include those of the first and second aspect.

Disclosed herein according to a sixth aspect of the invention is a non-transitory computer readable medium comprising the computer program according any feature of the fourth aspect. The non-transitory computer readable medium may comprise a memory unit of the processor or other computer-readable storage media for having computer readable program code stored thereon for programming a computer, e.g. a hard disk, a CD-ROM, an optical storage device, a magnetic storage device, Flash memory.

Disclosed herein according to a seventh aspect of the invention is provided a computer implemented method for implementing the method associated with the computer program of the fifth aspect. The above aspects of the invention may be combined in any suitable combination. Moreover, various features herein may be combined with one or more of the above aspects to provide combinations other than those specifically illustrated and described. Further objects and advantageous features of the invention will be apparent from the claims, from the detailed description, and annexed drawings.

The following describes a single general embodiment apparatus to which the various described embodiment features can be added without limitation, including those described in the summary of invention.

FIG. 1 shows a block diagram of an exemplary abstraction of electrical apparatus 2 to control plant growth according to the invention. The apparatus 2 can be suitably adapted for applications wherein large areas of plants are required to be treated, for example, applications in an agricultural environment or commercial environments (such as golf courses or sports pitches). Equally, it can be adapted for applications wherein smaller areas of plants are required to be treated, for example, private non-commercial use in the treatment of a garden of a home user. The apparatus 2 may be considered to comprise at a first level thereof: an electrical energy source 4; a processed electrical energy circuit 20; an electrical energy processing unit 6, which are described sequentially.

Electrical Energy Source

The electrical energy source 4 is operable to provide unprocessed electrical energy to the electrical energy processing unit 6 for conversion to processed electrical energy 36. The unprocessed electrical energy 34 may comprise any kind of electrical energy, such as a: direct current (DC), e.g. 12 V-24 V; or an alternating current (AC), e.g. 110 Vrms-240 Vrms at 50-60 Hz. The electrical energy source 4 may be fully or partially controlled by the electrical energy processing unit 6 e.g. by means of open-loop control or by means of closed-loop control, which comprises using an electrical energy source feedback and control signal to control and monitor aspects of the unprocessed electrical energy 34, e.g. the voltage and/or current and/or frequency by means of sensors, which is discussed in more detail further on. Alternatively the electrical energy source 4 has a separate control system, which comprises a user interface, such as actuators and/or a dedicated control system. The electrical energy source 4 can be arranged integrated with or discrete from the electrical energy processing unit 6. Moreover, the electrical energy source 4 may be arranged to supply one or more electrical energy processing units 6, which are commonly or independently controlled. Accordingly, it will be appreciated that the electrical energy source 4 may comprise various means, examples of which are discussed following.

Figure 2:
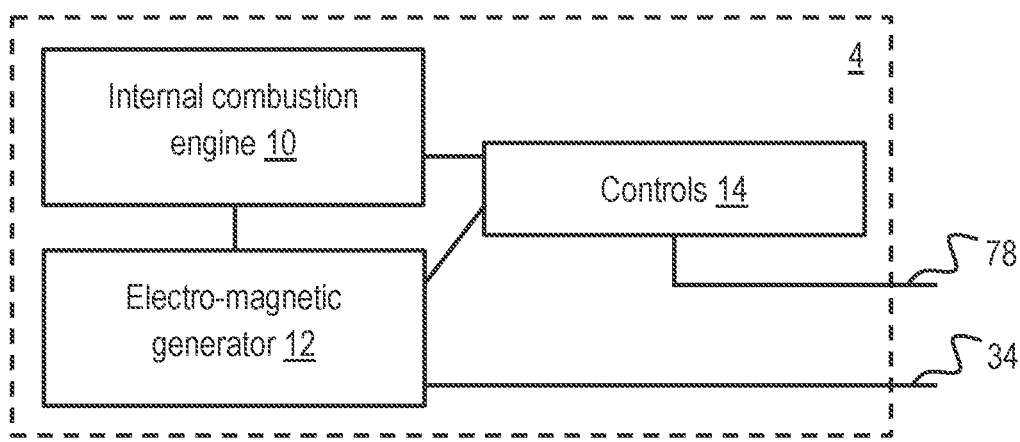
FIG. 2 is a block diagram of a first embodiment of an electrical energy source of the apparatus of FIG. 1.

In FIG. 2 shows in block form a preferred first embodiment of the electrical energy source 4, which is applicable to agricultural or home environments. Herein an engine-generator comprises an internal combustion engine 10 and an electro-magnetic generator 12. The engine 10 provides rotational energy to a rotor of the generator 12 that is configured to convert the rotational energy in to the unprocessed electrical energy 34, which is in turn supplied to the electrical energy processing unit 6.

The engine-generator further comprises controls 14 operable to control as input the engine 10 and/or generator 12. For example, the controls 14 may be operable to control one or more of the following input operational parameters of the engine 10: start-up/shut-down; angular velocity (of the rotor or engine); other operational parameters such as choke, and a disconnect switch of the generator 12. The controls 14 may comprise manual (for example, actuators) and/or automated means (for example, electrically operated actuators). Automated controls 14 are preferably controlled by the electrical energy processing unit 6. Control may be open-loop or closed-loop: e.g. the automated controls are controlled by means of an electrical energy source feedback and control signal 78 provided from sensors of the engine-generator such that if a difference between the output of a particular operation parameter and an associated reference value is a certain amount then the input is changed accordingly. The electrical energy source feedback and control signal 78 may comprise information relating to aspects of the engine-generator, such as one of more of the following: angular velocity; choke; oil level/temperature; water level/temperature; other operational parameters.

Figure 3:
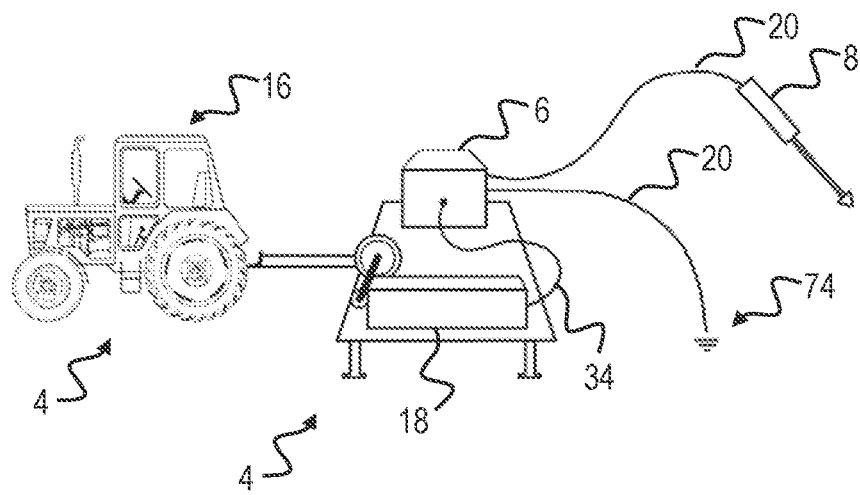
FIG. 3 is an illustrative diagram of a second embodiment of the electrical energy source of FIG. 1.

In FIG. 3 a second embodiment of an electrical energy source 4 is shown, which is suited to agricultural environments. Herein the electrical energy source 4 comprises a vehicle 16, such as a vehicle adapted for agricultural use (e.g. a tractor), which provides rotational drive from a power take-off shaft to a rotor of an electro-magnetic generator 18. Typically the power take-off shaft rotates at 540 rpm, and via a drive train drives the rotor to rotate at 1500-1800 rpm. The electro-magnetic generator 18 is configured to convert the rotational energy to the unprocessed electrical energy 34, which is in turn supplied to the electrical energy processing unit 6 for processing. Typically the electrical energy supplied from the electro-magnetic generator 18 has 110 Vrms-240 Vrms at 50-60 Hz. The electro-magnetic generator may be integrated as part of the vehicle, and thus the vehicle generates the unprocessed electrical energy 34.

In a third embodiment the electrical energy source 4 comprises a battery or a fuel cell. In this embodiment the unprocessed electrical energy 34 that is supplied to the electrical energy processing unit 6 is a direct current. An example of a suitable battery is a 12 V-24 V unit as used in the automotive industry. This embodiment is applicable to agricultural or home environments.

In a fourth embodiment the electrical energy source 4 comprises an AC line supply, such as a mains supply of a commercial or domestic property. Accordingly, the line supply may be 110-120 Vrms AC or 220-240 Vrms AC at 50-60 Hz. This embodiment is applicable to agricultural or home environments.

Processed Electrical Energy Circuit

The processed electrical energy circuit 20 comprises a circuit to transmit the processed electrical energy from the electrical energy processing unit 6. The circuit comprises electrodes of the applicator unit 8 and earth unit 74 and in use a treated plant and the ground. The applicator unit 8 and earth unit 74 will be described sequentially.

Applicator Unit

The applicator unit 8 is configured to receive processed electrical energy 36 from the electrical energy processing unit 6 and to transmit said electrical energy to one or more plants preferably by means of direct contact therewith.

The applicator unit 8 comprises one or a plurality of applicator electrodes, wherein the/each applicator electrode is configured to apply the processed electrical energy 36 to the/each plant, preferably via direct contact therewith. In an example comprising a plurality of applicator electrodes the applicator electrodes may be arranged in series or in parallel or a combination thereof with respect to the received electrical energy. Moreover, the electrical energy processing unit 6 may supply a separate electrical energy output for each or a group (i.e. 2 or more) of the plurality of applicator electrodes, for example, there is a separate transformer or transformer winding for each or the group of applicator electrode. In a similar fashion a single electrical energy processing unit 6 may supply one or a plurality of applicator units 8, e.g. the applicator units 8 are arranged in series or in parallel or a combination thereof with respect to the received electrical energy or the electrical energy processing unit 6 has a separate electrical energy output for each applicator unit 8.

The applicator electrode comprises an electrically conductive material e.g. copper, zinc, bronze, brass, aluminium or steel. The applicator electrode may further comprise an insulating dielectric material, which is operable to conduct the processed electrical energy 36 by capacitive action, such as an alumina or other ceramic, e.g. alumina or porcelain or a plastic such as Perspex$^R$. The dielectric material is arranged with respect to the electrically conductive material such that a treated plant receives the processed electrical energy 36 substantially or entirely via the dielectric material, e.g. an entire outer surface of the electrically conductive material is coated with the dielectric material or an exposed outer surface is coated. Typically, the dielectric material of the applicator electrode is a layer or coating, which is 0.5-2.5 mm thick. Advantageously, the dielectric material acts to reduce arcing. Moreover, the processed electrical energy 36 in the conductive material of the applicator electrode can be prevented from being in direct contact with a user. The processed electrical energy 36 can be effectively conducted through the dielectric material at the high-frequency, i.e. above 18 kHz or more particularly above 20 or 25 or 40 or 50 kHz.

In view of the above, it will be appreciated that the applicator unit 8 may comprise various arrangements. Embodiments with applicator unit(s) adapted for wide area coverage (e.g. by means of one or a combination of the following: numerous applicator units; numerous applicator electrodes; applicator units with electrodes for wide-area coverage) are suited to agricultural or commercial applications. Likewise, embodiments with applicator unit(s) adapted for small area coverage (e.g. by means of one or a combination of the following: single applicator units; single or multiple applicator electrodes; electrodes with small-area coverage) are suited to private non-commercial applications. Wide area coverage can be defined as comprising a ground treatment area of 50 cm$^2$ or 1 m$^2$ or more. Small area coverage can be defined as individual plants or a ground treatment area of up to 5 cm$^2$ or up to 10 cm$^2$. Examples of various applicator units 8 are discussed following.

Figure 4:
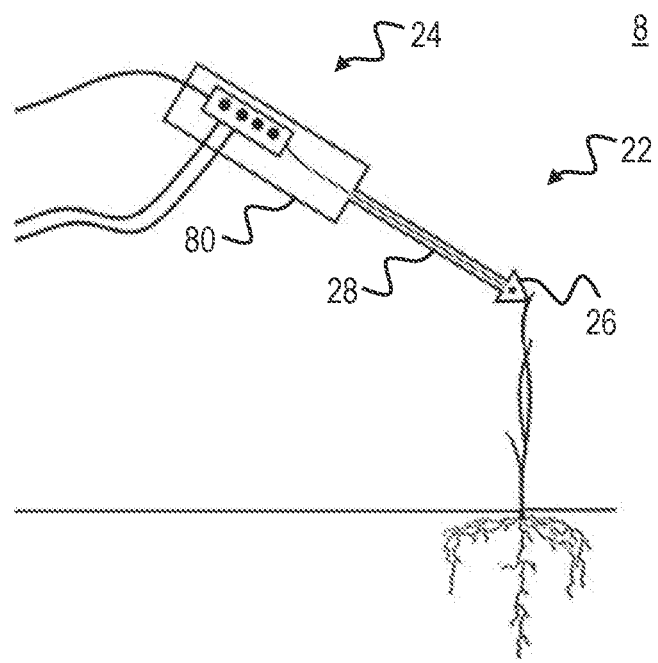
FIG. 4 is an illustrative diagram of a first embodiment of an applicator unit of the apparatus of FIG. 1.

In FIG. 4 a first embodiment of an applicator unit 8 is illustrated, which is generally applicable to private non-commercial environments. Herein the applicator unit 8 comprises an application head 22 and a body 24, which are described sequentially.

The application head 22 is for transmission of the electrical energy to a plant, and to this end comprises the applicator electrode 26 for direct contact therewith. The applicator electrode 26 can be shaped with various configurations, which are selected for the intended treatment regimen, for example: a rod for sweeping through areas of dense plants; a hook-shape for separating plants. The applicator electrode may be substantially rigid or compliant such that it is displaced during treatment.

The body 24 is for: connection of the applicator unit 8 to a chassis of the apparatus 2 in an example wherein the applicator unit 8 is fixed to a chassis of the apparatus; holding by a user in an example wherein the applicator unit 8 is discrete from a chassis and is movable independently therefrom. To this end the body 24 may comprise a connection/holding portion 80 and an extension portion 28. The connection/holding portion 80 is for said connection/holding of the applicator unit 8. The extension portion 28 provides an extended position of the head 22 with respect to the connection/holding portion 80 for convenience of use. At a proximal end of the extension portion 28 is arranged the connection/holding portion 80 and at a distal end is arranged the head 22. The connection/holding portion 80 and extension portion 28 are preferably made of an insulating material, such as a ceramic or plastic or rubber. Hence the extension portion 28 safely bridges the distance between the connection/holding portion 80 and the head 22. In the example wherein the applicator unit 8 is intended for holding by a user, the applicator unit 8 may have connected thereto a part of or all of a user interface (discussed later on), accordingly one or more of the features controlled by a user via the user interface may be controlled at the applicator unit 8.

Figure 5:
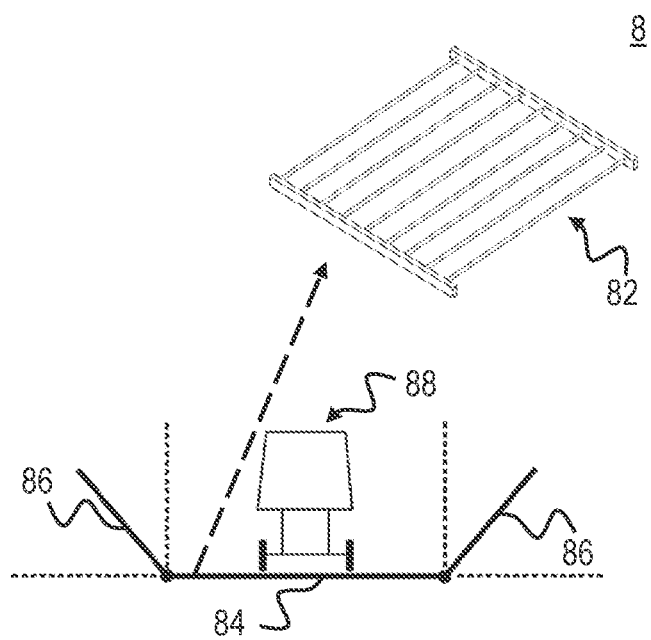
FIG. 5 is an illustrative diagram of a second embodiment of the applicator unit of FIG. 1.

In FIG. 5 a second embodiment of an applicator unit 8 is illustrated, which is generally applicable to agricultural environments. Herein the applicator unit 8 comprises a frame 82, which as shown may be formed of lateral and transverse members. The frame as shown may comprise a central portion 84 and first and second side portions 86. The side portions 86 can be pivotally or telescopically connected to the central portion such that they can be moved between an operating position and a stowed position for transit. The frame 82 can be supported by an agricultural vehicle 88, such as a tractor or a trailer. With such an example a suitable size is: 3 m×1.2 m in width and length respectively for the central portion; 1.5 m×1.2 m in width and length respectively for the side portions. The frame 82 is typically formed from an electrically conductive material, e.g. a metallic material such as steel. In this way the frame 82 in itself comprises the applicator electrode 26. The electrically conductive material is preferably hollow e.g. tube with a diameter of 12 mm.

Earth Unit

The earth unit 74 is configured to receive the processed electrical energy 36 from the applicator unit 8 via a plant and the earth, and is connected to the electrical energy source 4, generally via the energy processing unit 6 to provide a return path for the components therein and to complete a circuit that has a load comprising a treated plant and the earth. In use it is preferred that the earth electrode is arranged proximate the applicator unit 8 to reduce power loss into the earth (and for electrical safety). In a similar fashion to the applicator unit 8, the earth unit 74 may have connected thereto a part of or all of a user interface 42. Accordingly one or more of the features controlled by a user via the user interface may be controlled at the earth unit 74.

The earth unit 74 comprises an earth electrode 76 of electrically conductive material configured for electrical continuity with the ground. The electrically conductive material may comprise a metal such as copper, zinc, bronze, brass, aluminium or steel. Typically, the earth electrode 76 is 0.5-20 mm thick depending of the application and specific shape, e.g.: a 10-20 mm diameter rod or a 0.5-20 mm thick plate for the respective first and second embodiments discussed following.

In a first embodiment of the earth unit the earth electrode is in the form of an implement, which is configured to provide the return path when inserted into the ground, for example the earth electrode is formed as a spike or rod.

Figure 6:
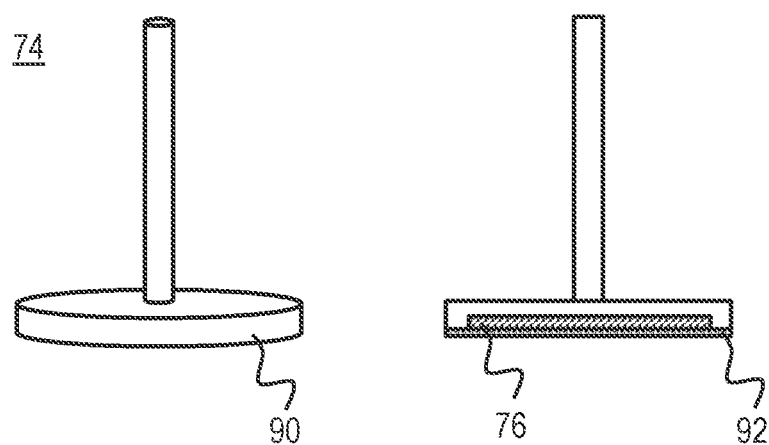
FIG. 6 is an illustrative diagram of an earth unit of the electrical weed killing apparatus of FIG. 1.
Figure 15:
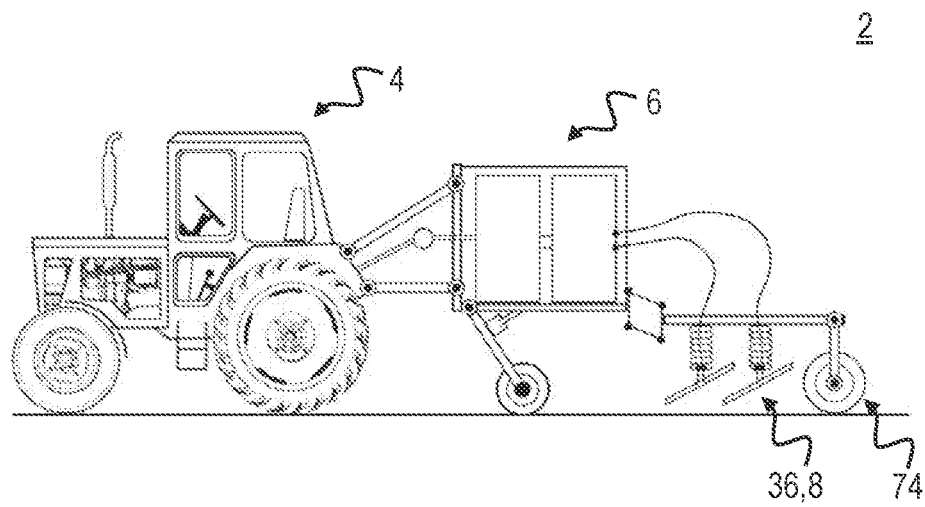
FIG. 15 is an illustration of the electrical weed killing apparatus of FIG. 1 adapted for use in an agricultural environment.

In a second embodiment of the earth unit 74 the earth electrode 76 is configured to provide a return path when resting on the ground. Generally, the earth electrode comprises a large surface area to aid electrical transmission. The earth electrode may comprise a substantially flat outer surface configured to stably rest against the ground, such as a plate or other suitable shape, e.g.: a circular plate, which may have diameter of 10-20 cm; a square plate, which may have a side length of 10-20 cm. An example of such an earth unit 74 is shown in FIG. 6, wherein an electrically insulating outer 90 surrounds a circular plate shaped earth electrode 76, which has an optional insulating dielectric material 92 discussed following. Alternatively the earth electrode may comprise (or be arranged around an outer periphery of) one or more rotary members, such as a wheel or roller, which is configured to rotate along the ground as the apparatus 2 is moved (such an example is shown in FIG. 15).

The earth electrode of the first or second embodiment may further comprise an insulating dielectric material, which is operable to conduct the processed electrical energy 36 by capacitive action, such as an alumina or other ceramic, e.g. alumina or porcelain or a plastic such as Perspex$^R$. The dielectric material is arranged with respect to the electrically conductive material such that the electrically conductive material receives the processed electrical energy 36 substantially or entirely via the dielectric material, e.g. an entire outer surface of the electrically conductive material is coated with the dielectric material or an exposed outer surface (that is to be inserted in or rest on the ground for the respective embodiments) is coated and optionally a rim adjacent thereto. Typically, the dielectric material of the earth electrode is a layer or coating, which is 0.5-2.5 mm thick. Advantageously, the processed electrical energy 36 in the conductive material of the earth electrode is prevented from being in direct contact with a user.

The second embodiment of the earth unit is particularly suited for use with an electrical energy processing unit 6 that produces processed electrical energy 36 waveforms with a frequency in the range of above 18 or 20 or 25 or 40 or 50 kHz. This is because the processed electrical energy 36 of this frequency can be relatively efficiently transmitted from the ground to the earth electrode without the need for insertion into the ground. As the frequency is increased the efficiency of the earth electrode in receiving the processed electrical energy 36 increases such that it may be made smaller and/or in embodiments that comprise the dielectric material the thickness thereof increased.

The second embodiment earth unit is advantageous in comparison to the first embodiment earth unit when, for example, treating plants at a first location and a distant second location: the earth electrode of the first embodiment earth unit requires extraction from the ground at the first location and insertion into the ground in operational proximity to the second location; comparatively the earth electrode of the second embodiment earth unit can be displaced from the first location to the second location by sliding or rolling it along the ground, thus obviating the steps of extraction and insertion. This functionality is particularly useful for applications wherein large areas of plants are required to be treated, for example, applications in an agricultural environment, wherein the apparatus 2 may be mounted to a vehicle driven system that is continuously is moved over the ground. Moreover, when treating certain ground, such as tarmac or hard-packed stone, it may not be possible to insert the first embodiment earth unit into the ground, and thus achieve adequate earth continuity. However, adequate earth continuity may still be achieved with the second embodiment earth unit since insertion is not essential.

The second embodiment earth unit when comprising an outer layer of insulating dielectric material, in comparison to the first embodiment earth unit, may be less effective in receiving the processed electrical energy 36 since the said capacitive action results in a slight voltage drop, however this can be compensated by increasing the voltage of the processed electrical energy 36.

Apparatus 2 to electrically control plant growth which use the second embodiment earth unit may be combined with other configuration applicator units, e.g. those that transmit the processed electrical energy to a plant not by direct contact therewith such as a spark transmission system as disclosed in JP H3-83534, and the related publication: 'Destruction of Weeds by Pulsed High-Voltage Discharges', A. Mizuno, T. Tenma and N. Yamano, Toyohashi University of Technology, 1990.

Electrical Energy Processing Unit

The electrical energy processing unit 6 is configured to: receive the unprocessed electrical energy 34, from the electrical energy source 4; process the unprocessed electrical energy 34 to the processed electrical energy 36; supply the processed electrical energy 36 between the applicator unit 8 and earth unit 74 for transmission to a plant. In general the aforesaid processing comprises processing to achieve the desired form of processed electrical energy 36, e.g. via conversion one or more of the: voltage; current; frequency; other optional aspects of the waveform.

The processed electrical energy 36 may comprise a periodic or aperiodic waveform, i.e. a waveform that continuously repeats with the repeating units therein having a constant or a varying period, e.g. a pulsed wave with a fixed duty cycle or a varying duty cycle. The shape of the repeating unit may be one of or a combination of one or more of the following forms: sine wave; saw-tooth wave; triangular wave; square wave; pulsed, e.g. DC pulsatile, half-wave rectified; other known form. The exact shape of the repeating unit may be an approximation of one of the aforesaid forms for reasons of distortion, e.g. overshoot/undershoot and the associated ringing and settle time. The repeating unit may be positive or negative or a combination thereof with respect to a reference value, which is typically 0 V.

Figure 7:
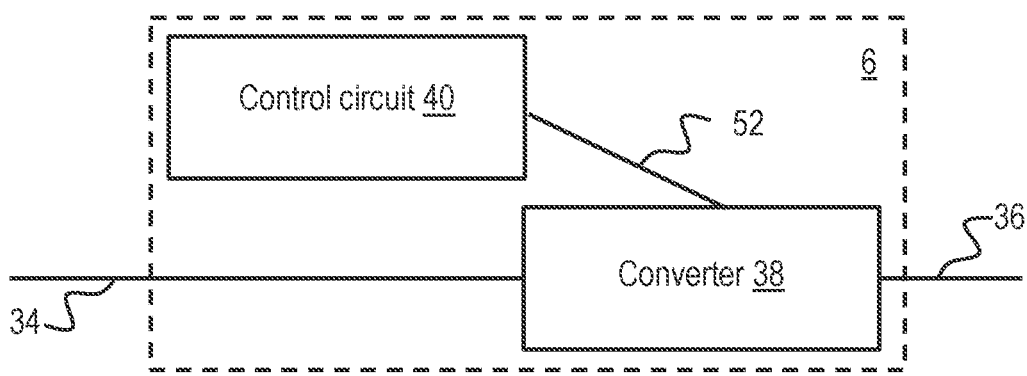
FIG. 7 is a block diagram showing an embodiment of an electrical energy processing unit of the apparatus of FIG. 1.

FIG. 7 shows a block diagram of the electrical energy processing unit 6 according to the invention. The electrical energy processing unit 6 may be considered to comprise at a second level of the apparatus 2: an optional control circuit 40; a converter 38, which are described sequentially.

The control circuit 40 typically comprises a processor and user interface (examples of which are discussed following). The control circuit 40 is operable to control, by means of a control signal 52 (which may be any suitable signal type, e.g. a digital, DC or AC signal), the converter 38 to convert the unprocessed electrical energy 34 to the desired form of processed electrical energy 36. The exact operation of the control circuit 40 depends on the conversion configuration of the converter 38, e.g.: in an example wherein the converter 38 is configured to convert only frequency (i.e. the unprocessed electrical energy 34 is supplied at the desired voltage) the control circuit 40 may supply a control signal to an electrically operated chopper switch of the converter 38, the switch arranged in series with the unprocessed electrical energy 34. Alternatively, in an example wherein the converter 38 is configured to convert only voltage and current (i.e. the unprocessed electrical energy 34 is supplied at the desired frequency and waveform) the control circuit 40 may supply a control signal to a variable transformer of the converter 38. Alternatively, the control circuit 40 may control via a control signal converter 38 that comprises a charge pump or boost converter or other suitable component.

In an example wherein the converter 38 provides a fixed operation on the unprocessed electrical energy (e.g. it comprises only a non-variable transformer for voltage and current conversion) it will be appreciated that a control circuit 40 may be obviated. However, generally the electrical energy processing unit 6 comprises a control circuit 40 when control of the said converter 38 is required.

Figure 8:
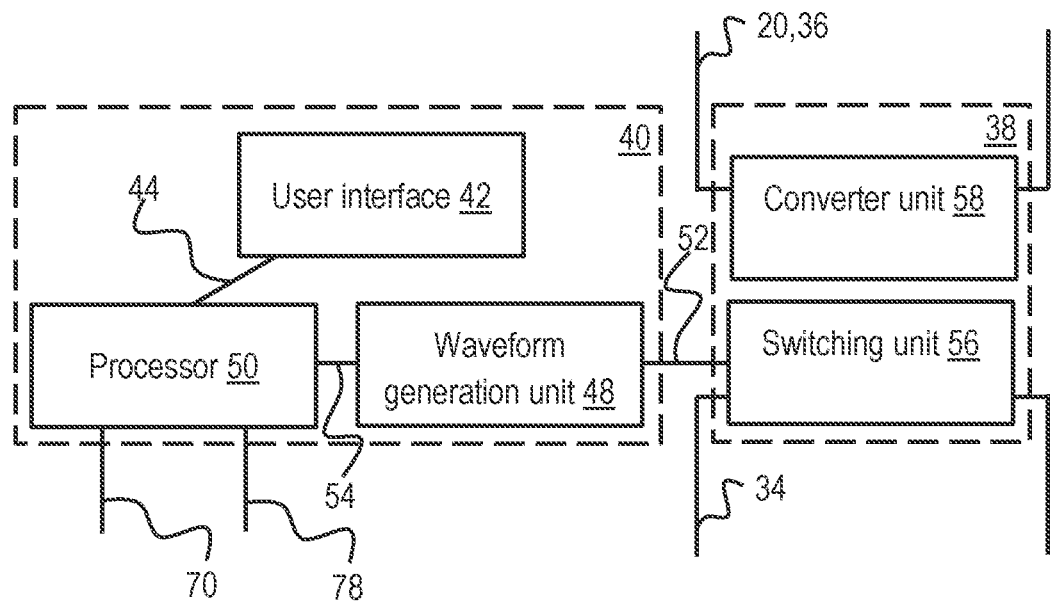
FIG. 8 is a block diagram showing an embodiment of a control circuit and a converter of the electrical energy processing unit of FIG. 7.

In a preferred example, which is illustrated in FIG. 8, the control circuit 40 is operable to generate a control signal comprising a waveform signal 52; the converter 38 is operable to convert, using the said waveform signal 52, the unprocessed electrical energy 34 to processed electrical energy 36, which has a waveform that corresponds to that of the waveform signal 52. In the said preferred example the control circuit comprises: a waveform generation unit 48; an optional processor 50; an optional user interface 42, which are described sequentially.

The waveform generation unit 48 is operable to generate the waveform signal 52, which may have various forms that are repetitive and can be periodic or aperiodic, e.g. a pulsed wave with a fixed duty cycle or a varying duty cycle. The shape of the repeating unit of the waveform may be one of or a combination of one or more of the following forms: sine wave; saw-tooth wave; triangular wave; square wave; pulsed, e.g. DC pulsatile, half-wave rectified; other known form. Moreover, the waveform signal may be positive or negative or a combination thereof with respect to a reference value, which is typically 0 V. The waveform generation unit 48 may for example comprise: a pulse width modulator (PWM); an arbitrary waveform generator (AWG); function generator; other suitable signal generator. The waveform generation unit 48 may be separate to or integrated with the processor 50 i.e. as a peripheral thereof.

The processor 50 generally is operable to control the converter 38 by means of the control signal 52. In the preferred example, which is illustrated in FIG. 8, the processor 50 is operable to control the waveform signal 52 via control of the waveform generation unit 48. In an example wherein the waveform generation unit 48 is configured to output a fixed waveform signal 52, the processor 50 can be obviated. Typically the processor 50 controls the form of the waveform of the processed electrical energy 36, e.g. via the form of the waveform signal 52, however the control element may be less sophisticated, e.g. on/off.

The processor 50 in a general example is operable to receive an input, for example, one or more of the following: commands from the user interface 42 via a user interface signal 44; the electrical energy source feedback and control signal 78 from the electrical energy source 4; a converter feedback signal 70 from the converter 38; unprocessed electrical energy 34. The input is processed according to program code (and/or programmed logic) stored on a memory unit of the processor 50 to determine an output. The output may be control via the control signal 52, e.g. open or closed-loop control, of one or more of the following aspects of the processed electrical energy 36: form; duty cycle, which is typically in the range of 0.05-0.45 (e.g. for a pulsed waveform); on/off; amplitude (e.g. to maintain the peak voltage at a particular magnitude for varying load); frequency; period; current; power; shape; other aspect. In the preferred example, which is illustrated in FIG. 8, the said control of the processed electrical energy 36 is typically via control of the corresponding waveform signal 52, e.g. via a control signal 54 to the waveform generation unit 48 and other associated units when present (such as a driver as discussed in the specific examples later on). The output may further be control of the unprocessed electrical energy 34 from the electrical energy source 4 by open-loop control or by closed-loop control by means of the electrical energy source feedback and control signal 78.

The processor 50 generally comprises memory, input and output system components, which are arranged as an integrated circuit, typically as a microprocessor or a microcontroller. The processor 50 may comprise other suitable integrated circuits, such as: an ASIC; a programmable logic device such as an FPGA; an analogue integrated circuit, such as a controller. For such devices, where appropriate, the aforementioned program code can be considered programed logic or to additionally comprise programmed logic. The processor 50 may also comprise a plurality of the aforementioned integrated circuits. An example is several integrated circuits arranged in communication with each other in a modular fashion e.g.: a slave integrated circuit to control the user interface 42 in communication with a master integrated circuit to control the waveform generation unit 48.

The processor 50 generally comprises a memory unit for storage of the program code and optionally data. The memory unit typically comprises: a non-volatile memory e.g. EPROM, EEPROM or Flash for program code and operating parameter storage; volatile memory (RAM) for data storage. The memory unit may comprise a separate and/or integrated (e.g. on a die of the processor) memory unit. The processor 50 may be idealised as comprising a control unit and an arithmetic logic unit or a plurality thereof, i.e. multiple processors.

The user interface 42 comprises hardware to enable a user to interface with the processor 50, by means of a user interface signal 44. A user may be able to control one or more of the outputs of the processor 50 via the user interface, e.g. the said aspects of the processed electrical energy 36 including: optional high, medium and low power settings (e.g. low power may be 50% of the high power and medium power may be 75% of the high power); optionally a reset power setting. Moreover, in embodiments comprising a plurality of applicator units 8 and/or applicator electrodes 26, the aforementioned aspects of the processed electrical energy 36 may be controlled via the user interface 42 for the applicator units 8 and/or applicator electrodes individually or in groups. A user may further be able to control one or more of the following aspects of the electrical energy source 4/unprocessed electrical energy 34 via the user interface 42: on/off; voltage; current; other aspects that will depend on the particular embodiment of the electrical energy source 4.

The hardware of the user interface 42 may comprise any suitable device(s), e.g. one or more of the following: buttons, such as a joystick button; LEDs; graphic or character LDCs; graphical screen with touch sensing or screen edge buttons; on/off switch. The user interface 42 can be formed as one unit or a plurality of discrete units, and may be arranged remote from the other third level components of the control circuit 40, e.g. in apparatus 2 adapted for use in an agricultural environment it may be arranged in the cabin of an agricultural vehicle.

The user interface signal 44 is transmitted between the user interface 42 and the processor 50 by means of cabled media or wireless media or a combination thereof, e.g.: a wired connection, such as RS-232, USB, I²C, Ethernet define by IEEE 802.3; a wireless connection, such as wireless LAN (e.g. IEEE 802.11) or near field communication (NFC) or a cellular system such as GPRS or GSM. For more sophisticated media the processor 50 and user interface 42 can be operatively connected to (or comprises as a peripheral) the relevant communication interfaces. The processor 50 may be operatively connected to (or comprises as a peripheral) a web server or a network router and the user interface 42 may comprise a program such as a web browser executed by a communication device such as a: PDA; tablet; laptop; smartphone; PC; or other suitable device.

The components that comprise the control circuit 40 are typically powered by the unprocessed electrical energy 34 from the electrical energy source 4 following conversion to a suitable voltage, e.g. 10 V DC. They may alternatively be powered by a separate electrical energy source.

The converter 38 will now be discussed and, as illustrated in FIG. 7, is configured to: generally receive the control signal 52 from the control circuit 40; receive the unprocessed electrical energy 34 from the electrical energy source 4; convert, generally using the control signal 52, the unprocessed electrical energy 34 to the desired form, e.g. via conversion one or more of the: voltage; current; frequency; other optional aspects of the waveform; transmit said processed electrical energy 36 to the processed electrical energy circuit 20.

The converter 38 may have various configurations depending on its mode of operation, e.g.: in an example wherein the converter 38 converts frequency (i.e. the unprocessed electrical energy 34 is at the desired voltage) the converter 38 comprises a converter unit in the form of an electrically operated chopper switch, the switch arranged in series with the unprocessed electrical energy 34. Alternatively, in an example wherein the converter 38 converts voltage and current (i.e. the unprocessed electrical energy 34 is at the desired frequency) the converter 38 comprises a converter unit in the form of a variable or non-variable transformer. In further examples the converter unit may comprise a charge pump or boost converter or other suitable electrical component.

Figure 9:
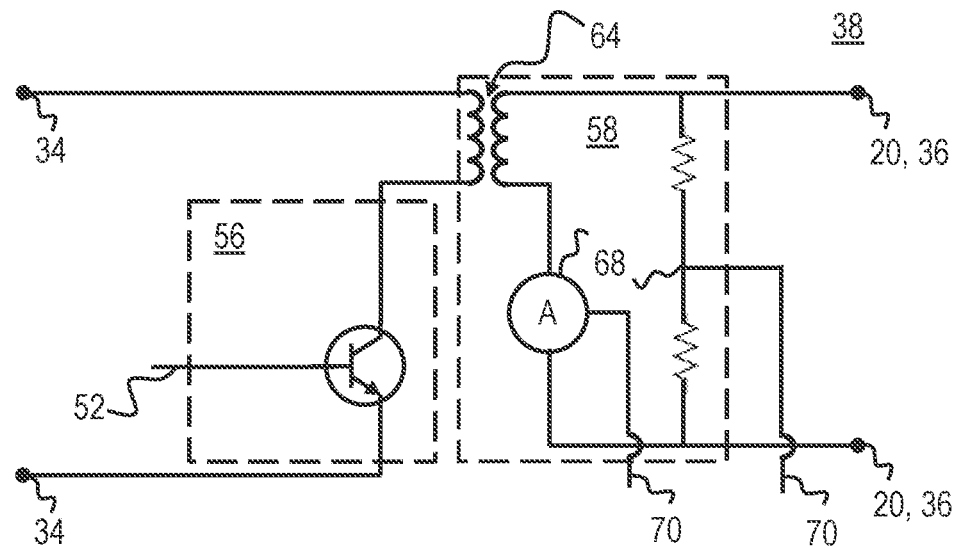
FIG. 9 is a schematic diagram showing an embodiment of a converter of the electrical energy processing unit of FIG. 7.

In the preferred example, which is illustrated block form in FIG. 8 and schematically in FIG. 9, the converter 38 comprises: a switching unit 56; a converter unit 58, and is operable to convert voltage, current and frequency, and other optional aspects to derive the desired the waveform of the processed electrical energy 36. The switching unit 56 and converter unit 58 will be described sequentially.

The switching unit 56 is configured to receive the control signal 52 and, using the control signal 52, switch the unprocessed electrical energy 34 at a desired frequency through the converter unit 58. Accordingly, the switching unit 56 generally comprises an electrically operated switch, an example of which is one or more (e.g. a Darlington pair or other arrangement) transistor. The transistor is generally arranged with: a base connected to the control signal 52; an emitter grounded; a collector connected to the unprocessed electrical energy 34 via the converter unit 58, although various other arrangements are possible. Other forms of electrically operated switch may be used, such as a MOSFET, IGBT or triac.

The converter unit 58 is operable to receive the switched unprocessed electrical energy 34 and to transform its voltage to a desired magnitude to determine the processed electrical energy 36. Accordingly, the converter unit 58 generally comprises: a step-up transformer 64 having a primary winding arranged in series with the switched unprocessed electrical energy 34; a secondary winding arranged in series with the applicator unit 8 and earth unit 74, thereby defining a circuit comprise a treated plant.

The converter 38 may further comprise one or more sensor(s) 68 for monitoring and/or controlling aspects of the processed electrical energy 36, for example, the voltage and/or current. The sensor(s) 68 provide a converter feedback signal 70 (which may be any suitable signal type, e.g. a digital, DC or AC signal), to the processor 50, typically for closed-loop control. As an alternative to use in closed-loop control (or in addition) the converter feedback signal 70 may be stored on the memory unit so that it may subsequently be analysed.

The electrical energy processing unit 6 is typically configured to generate processed electrical energy 36 that has a waveform with a peak voltage in the range of 1 kV to 30 kV: it may be specifically configured or user controllable to generate a waveform with any peak voltage therebetween. Generally, the voltage is about 4-8 kV.

The electrical energy processing unit 6 is typically configured to generate processed electrical energy 36 that has a waveform that repeats continuously with a frequency of 18 kHz to 5 MHz: it may be specifically configured or user controllable to generate a waveform that repeats with any frequency therebetween. Generally, the frequency is about 20-75 kHz.

As electrical current flows through a plant, the plant can be killed by the current due to heat generated by the plant's resistance to electron flow. In more detail, as the current flows it damages the cellular structure of the plant and water is released. The increased water has the effect of reducing the resistance: this allows more current to flow so more damage is done, reducing the resistance still further, so more current flows and so on. The current therefore generally rises with time. The initial current required to kill a particular plant will vary considerably depending on the type of plant, its moisture content, and the moisture of the air, soil etc. The electrical energy processing unit 6 is typically configured to generate processed electrical energy 36 that has initial current of at least 10 mA, although typically a higher initial current is used.

The electrical energy processing unit 6 is typically configured to generate processed electrical energy 36 that has an initial power of at least 5 W. The initial power may vary depending on the embodiment of the electrical energy source 4 that the electrical energy processing unit 6 is configured to operate with, e.g.: for the first or second embodiment the initial power may be 3-6 kW for 3-5 kV; for the third embodiment the initial power may be 500-2000 W for 2.5-4 kV; for the fourth embodiment the initial power may be 2-3 kW for 2.5-4 kV. Generally, for apparatus 2 intended for agricultural/commercial use the electrical energy processing unit 6 and electrical energy source 4 produce processed electrical energy 36 with an initial power of 10-60 kW at 5-20 kV. Generally, for apparatus 2 intended for private non-commercial use, the electrical energy processing unit 6 and electrical energy source 4 produce an initial power of 100-3000 W at 2-5 kV.

The electrical energy processing unit 6 is typically configured to generate processed electrical energy 36 that can kill a plant with a treatment time of at least 10 milliseconds. It will be appreciated that a small treatment time, such as 10 milliseconds will be applicable to small plants, whereas large plants will take longer, such as 5-6 seconds.

The processed electrical energy 36 may be controlled by the processor 50 in various ways, such as control over (or through) the load (comprising a treated plant and the earth) of the: voltage; current; power, examples of which will now be discussed.

The following examples of processed electrical energy 36 control may be applied to apparatus 2 that generate lower frequency processed electrical energy 36, such as processed electrical energy 36 with any voltage and frequency suitable for killing a plant, e.g. 50-60 Hz (as disclosed in U.S. Pat. No. 4,338,743) up to the above preferred range (it will be appreciated that the above electrical energy processing unit 6 could be configured to produce this processed electrical energy, e.g. by generation of the appropriate control signal 52). Moreover, the control may be applied to apparatus 2 with other configuration applicator units, e.g. those that transmit the processed electrical energy to a plant without direct contact therewith, such as a spark transmission system as disclosed in JP H3-83534, and the related publication: 'Destruction of Weeds by Pulsed High-Voltage Discharges', A. Mizuno, T. Tenma and N. Yamano, Toyohashi University of Technology, 1990.

Example 1: Control of Voltage Generally to Maintain a Constant Voltage Over the Load As the load (i.e. the current drawn) between the applicator unit 8 and earth unit 74 decreases the voltage over the load generally increases. In a similar fashion, as the load between the applicator electrode 26 of the applicator unit 8 and earth unit 74 increases the voltage over the load generally decreases. Accordingly, the voltage of the processed electrical energy 36 can be maintained at particular value or range (i.e. a range defined by a first and/or second predetermined value) by open loop control or by closed loop control (e.g. by monitoring the voltage of the processed electrical energy 36 using the converter feedback signal 70). The voltage of the processed electrical energy 36 can be increased in response to a decreasing voltage by increasing its duty cycle (or amplitude) or decreased in response to an increasing voltage by decreasing its duty cycle (or amplitude). In this way the voltage is kept as high as possible to optimise the duration (e.g. the speed) of the process.

As an example of this process: the voltage may be maintained at 2 kV or 5 kV or 10 kV, including ±5% or 10% thereof.

Example 2: Control of Current Generally to Maintain a Constant Current Through the Load During treatment of a plant, the current through the plant generally increases due to the resistance of the plant decreasing as damage to the cellular structure occurs. Accordingly, the current of the processed electrical energy 36 can be maintained at particular value or range (i.e. a range defined by a first and/or second predetermined value) by open loop control or by closed loop control (e.g. by monitoring the current of the processed electrical energy 36 using the converter feedback signal 70). The current of the processed electrical energy 36 can be increased in response to a decreasing current by increasing its duty cycle (or amplitude) or decreased in response to an increasing current by decreasing its duty cycle (or amplitude).

The aforementioned current control may only be applied to a gradually increasing current once it achieves one of the said predetermined values.

In this way overload of the converter can be avoided. Moreover, the voltage is kept as high as possible whilst the current is rising to optimise the duration (e.g. the speed) of the process.

As an example of this process: for a 500 W unit configured to generate processed electrical energy 36 at 5 kV, once the processed electrical energy 36 achieves a current of 0.1 A, the voltage of the processed electrical energy 36 is reduced, to maintain the current of 0.1 A or 0.1 A±5%.

Example 3: Control of Power to Maintain Generally a Constant Power Through the Load During treatment of a plant, the current through the plant generally increases due to the resistance of the plant decreasing as damage to the cellular structure occurs. Accordingly, the power of the processed electrical energy 36 can be maintained at particular value or range (i.e. a range defined by a first and/or second predetermined value) by open loop control or by closed loop control (e.g. by monitoring the current and voltage of the processed electrical energy 36 using the converter feedback signal 70). The voltage of the processed electrical energy 36 can be increased in response to a decreasing current by increasing its duty cycle (or amplitude) or decreased in response to an increasing current by decreasing its duty cycle (or amplitude).

The aforementioned power control may only be applied to a gradually increasing power once it achieves one of the said predetermined values.

In this way overload of the converter can be avoided. Moreover, the voltage is kept as high as possible whilst the current is rising to optimise the speed of the process.

As an example of this process: once the processed electrical energy 36 achieves a current of 0.1 A, the voltage of the processed electrical energy 36 is reduced to maintain the power at a first predetermined amount of 500 W or 500 W±5%; as the current continues to increase the voltage is reduced to maintain 500 W or 500 W±5%, e.g. as the current rises to 0.2 A the voltage is reduced to 2.5 kV, and at 0.5 A the voltage is reduced to 1 kV.

Specific Example Circuits for the Electrical Energy Processing Unit

It will be appreciated that the aforementioned circuits of the electrical energy processing unit 6 may comprise various electrical components, some specific examples of which are provided following.

Embodiment 1: Pulse Width Modulated Forward Convertor

Figure 10:
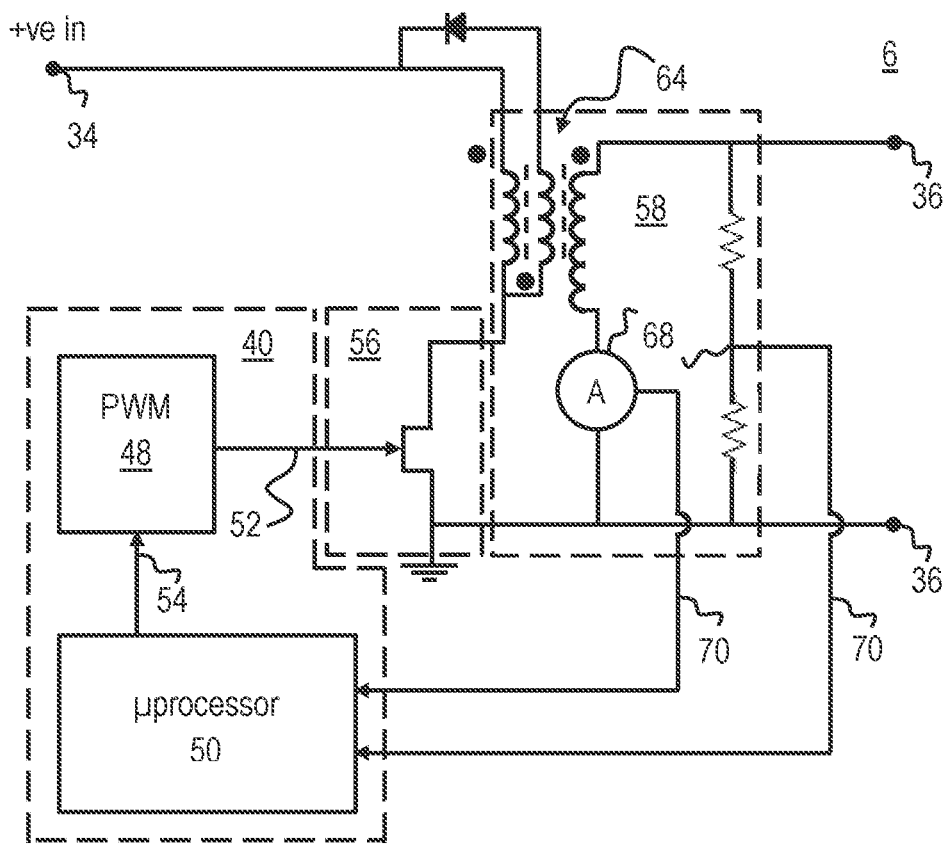
FIG. 10 is a schematic diagram of a first embodiment of the electrical energy processing unit of FIG. 1.

A first embodiment of the electrical energy processing unit 6 is shown in FIG. 10, wherein the control circuit 40 comprises a processor 50 that is a microprocessor and a waveform generation unit 48 that is a pulse width modulator (PWM). The microprocessor controls the PWM by means of control signal 54 that is decoded by the PWM and converted to a square wave. The duty cycle and frequency of the square wave are controlled by the microprocessor via the control signal 54. The control signal 54 may be any suitable signal type, e.g. a digital, DC or AC signal. The PWM outputs the control signal 52 to the converter 38.

The converter 38 comprises a switching unit 56 that is a MOSFET, which is arranged with: the gate connected to the control signal 52 from the PWM; the source grounded; the drain connected to the unprocessed electrical energy 34. The converter 38 further comprises a converter unit 58, which has a transformer 64 with a primary and secondary winding arranged as described in the general example above and a reset winding to rid a core of the transformer of stored energy during the off cycle to avoid/reduce saturation. The converter 38 has sensors 68 consisting of a current sensor in series with the load and a divider arranged over the load for voltage measurement. Accordingly a converter feedback signal 70 from the sensors 68 provides voltage and current information to the processor 50.

The control signal 52 switches the MOSFET 56 to effect switching of the unprocessed electrical energy 34 across the primary winding of the transformer 64, which is transformed at the secondary winding to the processed electrical energy 36.

The first embodiment of the electrical energy processing unit 6 is generally suitable for operation at less than 300 Watts.

Embodiment 2: Linear Amplifier

Figure 11:
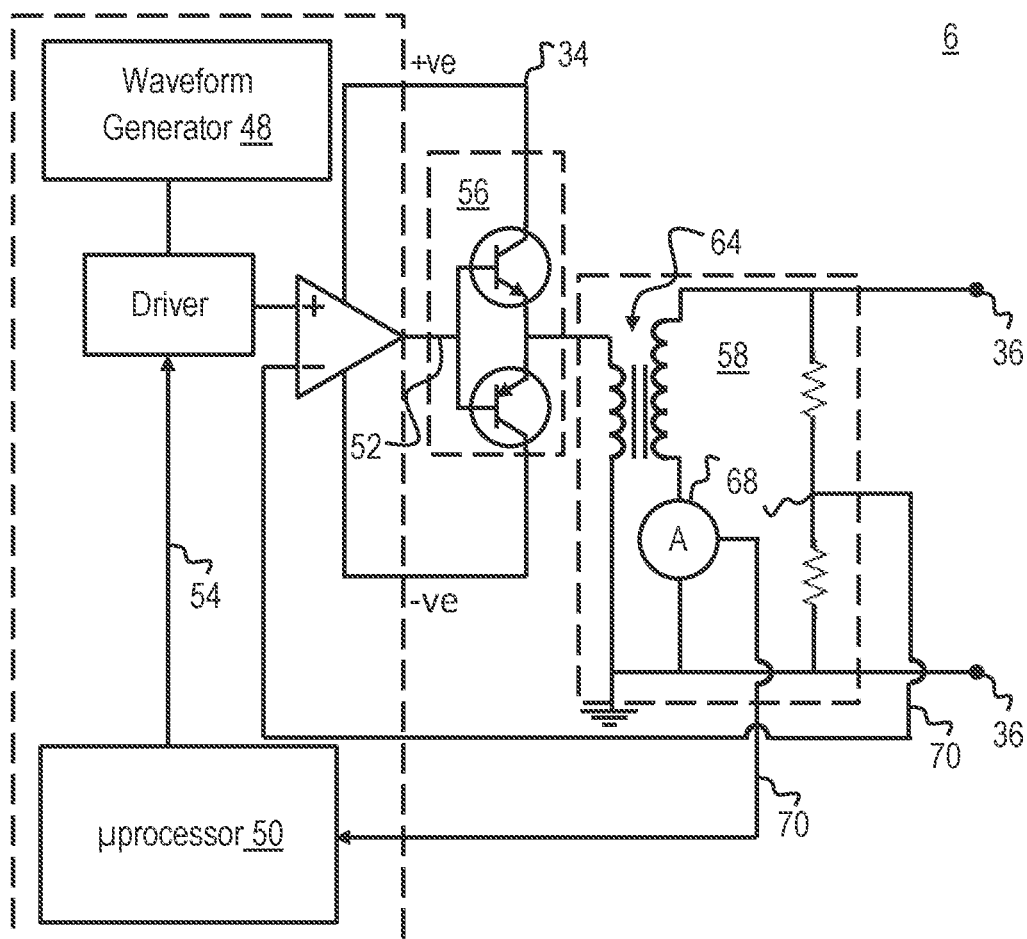
FIG. 11 is a schematic diagram of a second embodiment of the electrical energy processing unit of FIG. 1.

A second embodiment of the electrical energy processing unit 6 is shown in FIG. 11, wherein the control circuit 40 comprises: a processor 50 that is a microprocessor; a waveform generation unit 48; an op-amp and associated driver. The microprocessor 50 controls the driver by means of the control signal 54. The waveform generation unit 48 outputs a control signal to the driver, which may for example be a sine wave (or other one of the aforementioned waves). Aspects of the control signal (e.g. form and frequency) output from the waveform generation unit 48 may be fixed or controllable by the microprocessor 50. The driver transfers the control signal to the non-inverting input of the op-amp where it is amplified to the required level, as will be discussed.

The converter 38 comprises a switching unit 56 that is a NPN transistor and a PNP transistor, which are arranged with: the bases connected in parallel to the control signal 52 from the op-amp; the emitters connected to each other and to the primary winding of the transformer; the collector of the NPN transistor connected to the positive power supply of the op-amp; the collector of the PNP transistor connected to the negative power supply of the op-amp. The converter 38 further comprises a converter unit 58, which has a transformer 64 with a primary and secondary winding arranged as described in the general example above. The converter 38 has sensors 68 consisting of a current sensor in series with the load and a divider arranged over the load for voltage measurement. The current sensor 68 is connected to the microprocessor 50 such that the converter feedback signal 70 provides current and voltage information thereto. The voltage sensor 68 is connected to the inverting input of the op-amp such that the converter feedback signal 70 provides voltage information thereto.

Figure 12A:
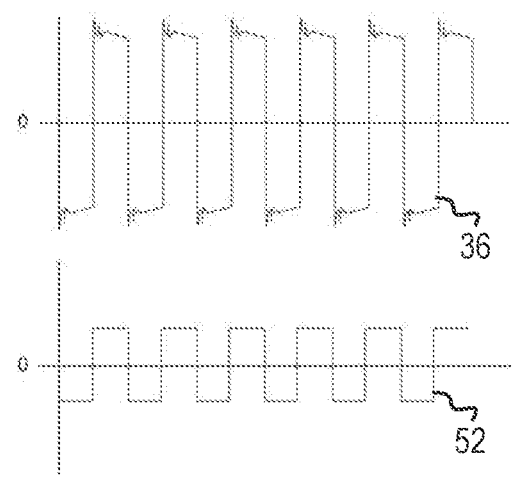
FIG. 12*a* is an illustration of a waveform signal and a corresponding processed electrical energy output from the first embodiment of the electrical energy processing unit.
Figure 12B:
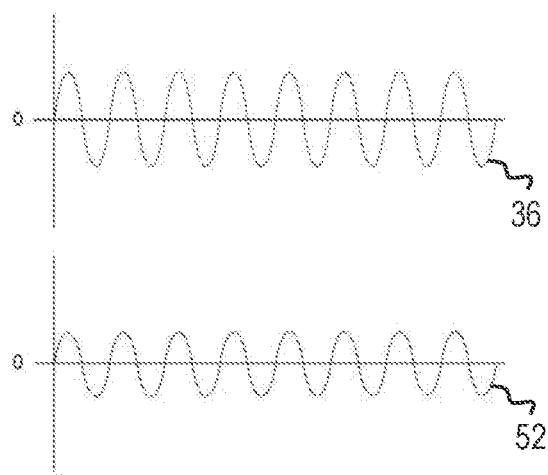
FIG. 12*b* is an illustration of a waveform signal and a corresponding processed electrical energy output from the second embodiment of the electrical energy processing unit.

The control signal 52 switches the NPN and PNP transistors when positive or negative respectively to effect switching of the unprocessed electrical energy 34 across the primary winding of the transformer 64 in accordance with the control signal 52. As shown in FIG. 12*a-b*, the processed electrical energy 36 at the secondary winding of the transformer 64 is substantially an amplification of the control signal 52. More particularly, FIG. 12*a* shows the amplification of a square control signal 52 and FIG. 12*b* shows the amplification of a sine control signal 52. The voltage feedback of the converter feedback signal 70 to the inverting input of the op-amp enables the maintaining by the op-amp of a constant voltage as the load (e.g. the resistance of a treated plant) varies. The microprocessor may comprise program code to effect control of the driver to maintain or decrease the gain of the op-amp in accordance with the current feedback of the converter feedback signal 70 to the microprocessor.

The second embodiment of the electrical energy processing unit 6 is generally suitable for operation at less than 1500 Watts.

Embodiment 3: Push-Pull System

Figure 13:
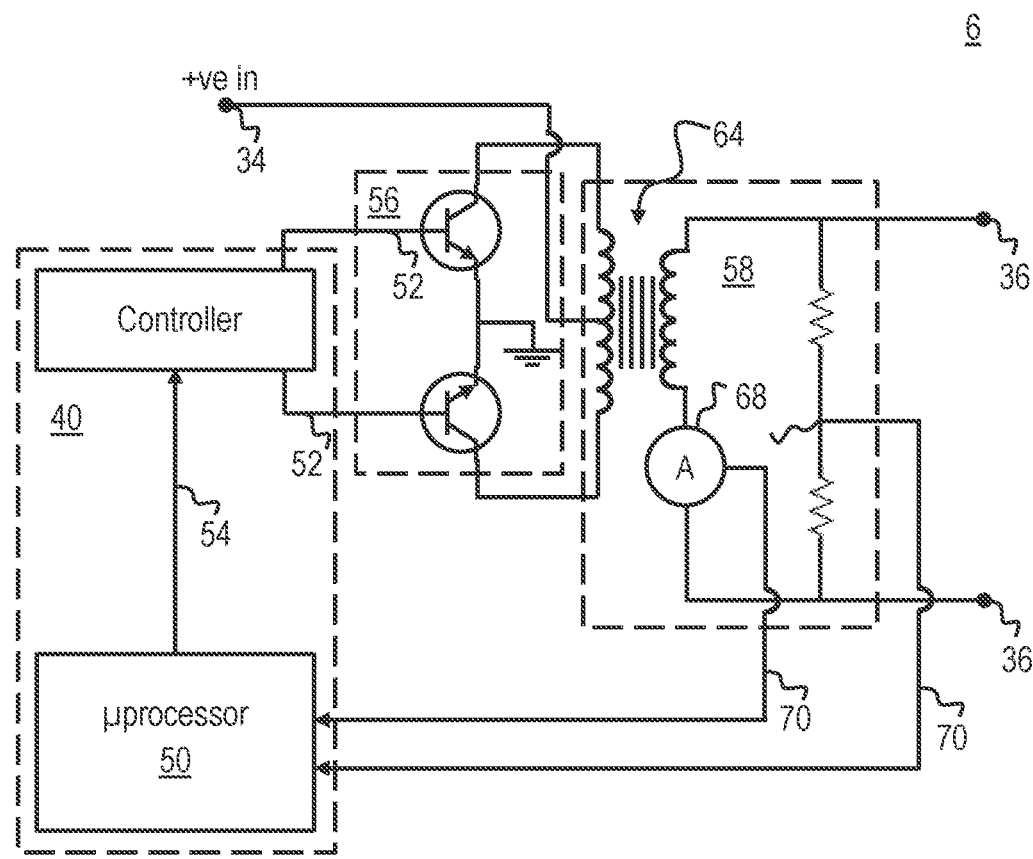
FIG. 13 is a schematic diagram of a third embodiment of the electrical energy processing unit of FIG. 1.

A third embodiment of the electrical energy processing unit 6 is shown in FIG. 13, wherein the control circuit 40 comprises a processor 50 that is a microprocessor and a waveform generation unit 48 that is a controller with an integrated waveform generator. The microprocessor 50 controls the controller by means of the control signal 54 that is decoded by the controller to control the control signal 52. The controller is configured to generate a control signal 52 that comprises a first and second channel that is supplied to the respective first and second transistors of the converter 38. The first and second channel waveforms are both square waves, the duty cycle and frequency of which is controlled by the microprocessor via the control signal 54. The control signal 54 may be any suitable signal type, e.g. a digital, DC or AC signal.

The converter 38 comprises a switching unit 56 that comprises a first and second NPN transistor, which are arranged with: the base of the first transistor connected to the first channel control signal 52 from the controller; the base of the second transistor connected to the second channel control signal 52 from the controller; the emitters grounded; the collector of the first transistor connected to first primary windings of the transformer 64; the collector of the second transistor connected to second primary windings of the transformer 64.

The converter further comprises a converter unit 58, which comprises the transformer 64 with a secondary winding arranged as described in the general example above. The unprocessed electrical energy 34 is connected to both primary windings of the transformer. The primary windings are arranged such that their energising causes flux to flow in the core in respective first and second opposed directions. Accordingly, the transistors are sequentially switched by the first and second channel control signals to effect the transformation of processed electrical energy 36 that corresponds to the sum of the first channel control signal with the out of phase second channel control signal.

The converter 38 has sensors 68 consisting of a current sensor arranged in series with the load and a divider arranged over the load for voltage measurement. Accordingly a converter feedback signal 70 from the sensors 68 provides voltage and current information to the processor 50.

The third embodiment of the electrical energy processing unit 6 is generally suitable for operation at less than 1000 Watts.

Embodiment 4: Full Bridge Converter

Figures 14, 16:
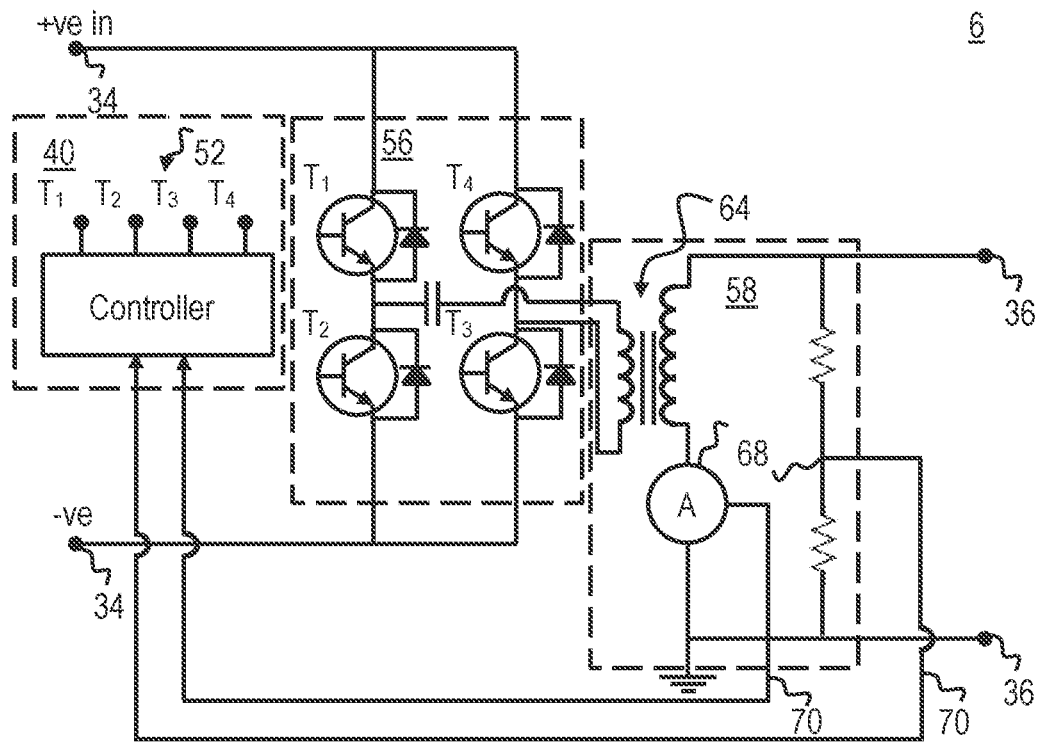
FIG. 14 is a schematic diagram of a fourth embodiment of the electrical energy processing unit of FIG. 1.
FIG. 16 shows tabulated experimental results from electrical weed killing apparatus according to the invention.

A fourth embodiment of the electrical energy processing unit 6 is shown in FIG. 14, wherein the control circuit 40 comprises a processor and waveform generator integrated as a controller. The controller is configured to generate a control signal that comprises a first, second, third and fourth channel that is supplied to the respective first, second, third and fourth transistors of the converter. The first, second, third and fourth channel waveforms are all square waves, the duty cycle and frequency of which is controlled by the controller.

The converter comprises a switching unit 56 that comprises the first T1, second T2, third T3 and fourth T4 NPN transistors. The transistors are arranged to in series pairs: T1 and T2; T3 and T4. The converter further comprises a converter unit 58, which comprises a transformer 64 with a secondary winding arranged as described in the general example above. The primary winding of the transformer is connected across the junctions of the series pairs. The controller supplies the control signal that sequentially switches opposed transistor pairs: T1 and T3; T2 and T4. The current therefore travels via the said opposed pairs to effect an alternating current across the primary winding. Accordingly, the processed electrical energy 36 transformed corresponds to the sum of the first (and third) channel control signal with the out of phase second (and fourth) channel control signal.

The converter 38 has sensors 68 consisting of a current sensor arranged in series with the load and a divider arranged over the load for voltage measurement. Accordingly a converter feedback signal 70 from the sensors 68 provides voltage and current information to the controller.

The fourth embodiment of the electrical energy processing unit 6 is generally suitable for operation at above 1000 Watts.

General Example of Apparatus for Agriculture

FIG. 15 shows and overall example of the apparatus 2 when adapted for agriculture, wherein: the electrical energy source 4 comprises a vehicle according to the second embodiment; the electrical energy processing unit 6 is arranged on a towed vehicle; a plurality of applicator units 8 extend from the vehicle; the earth unit 74 comprises a rotary member according to the second embodiment.

Experimental Results

Experimental results were obtained by the application of electrical energy according to the invention and the prior art to small samples of 5-10 French Marigold, each sample was grown under the same conditions for 8 weeks. In particular: the voltage (peak) was varied from 3 kV-6 kV in 1 kV increments; the frequency was varied generally from 5 kHz-50 kHz in 5 kHz increments; the electrical energy was applied for 1 second. The subsequent response of the plant was observed for the period of 4 days.

Referring to FIG. 16 it can be seen that although there is a large amount of variation in the experimental results (which would be improved by an increased sample size) the kill efficacy (in %) is maintained above around 18-25 kHz. It is expected that if the sample size/range of plants tested were to be increased, the potential advantage of high-frequency would be more pronounced. At around 3 kV, which may be considered a threshold voltage, there is insufficient electrical energy to reliably kill the sample at all frequencies. A method of treatment of a plant may therefore comprise establishing a threshold voltage. The method may also comprise determining a treatment time. The threshold voltage and time may be determined from experimental data, i.e. a database, and/or predicted.

LIST OF REFERENCES

2 Apparatus to control plant growth
4 Electrical energy source
34 Unprocessed electrical energy
Embodiment 1
10 Internal combustion engine
12 Electro-magnetic generator
14 Controls
Embodiment 2
16 Vehicle
18 Electro-magnetic generator
6 Electrical energy processing unit
36 Processed electrical energy
38 Converter
56 Switching unit
58 Converter unit
64 Transformer
68 Sensor
70 Converter feedback signal
40 Control circuit
48 Waveform generation unit
52 Control signal
50 Processor
78 Electrical energy source feedback and control signal
54 Control signal
42 User interface
44 User interface signal
20 Processed electrical energy circuit
74 Earth unit
76 Earth electrode
90 Electrically insulating outer
92 Insulating dielectric material
8 Applicator unit
Embodiment 1
22 Head
26 Applicator electrode
24 Body
80 Mounting/holding portion
28 Extension portion
Embodiment 2
82 Frame (applicator electrode 26)
84 Central portion
86 Side portion
88 Vehicle

What is claimed is:

1. An apparatus to electrically kill a plant or at least attenuate plant growth, the apparatus comprising:
    an electrical energy processing unit comprising a converter operable to receive unprocessed electrical energy from an electrical energy source, to convert the unprocessed electrical energy to processed electrical energy having an electrical current and to transmit the processed electrical energy between an applicator electrode of an applicator unit and an earth electrode of an earth unit,
    the applicator unit comprising the applicator electrode, wherein the applicator electrode comprises an electrically conductive material, the applicator unit being electrically coupled to the converter of the electrical energy processing unit wherein the applicator unit is operable to receive the processed electrical energy and to apply the processed electrical energy directly to at least a portion of a plant that extends above the ground; and
    the earth unit comprising the earth electrode, wherein the earth electrode comprises an electrically conductive material, the earth unit being electrically coupled to the converter, wherein the earth unit is operable to receive the processed electrical energy transmitted from the applicator unit through a load comprising the plant, and wherein the earth electrode comprises a surface that is configured to be placed substantially planar to a surface of the ground so as to electrically couple the earth unit to the ground; and
    wherein the applicator electrode is configured for direct transmission of the processed electrical energy to at least part of the plant above ground such that the electrical current travels through the at least part of the plant above ground as part of a circuit and the electrical current returns to the earth electrode through the surface of the ground, wherein the processed electrical energy comprises a waveform with a frequency of at least 18 kHz and with a peak voltage of at least 1 kV and with an electrical current of at least 10 mA rms.

2. The apparatus of claim 1, wherein the electrical energy processing unit is configured to produce processed electrical energy that comprises a a power of at least 5 W.

3. The apparatus of claim 1, wherein the electrical energy processing unit is configured to produce processed electrical energy that is operable to kill a plant or at least partially attenuating plant growth with a treatment time of at least 10 milliseconds.

4. The apparatus of claim 1, wherein the electrical energy processing unit further comprises a control circuit operable to control the converter to convert the unprocessed electrical energy to the processed electrical energy, wherein the control circuit is configured to control an aspect of the processed electrical energy comprising one or a combination of the:
    voltage; current; power, the said aspect controlled to be:
        maintained substantially at a predetermined value; or
        below or above a predetermined value; or
        within a particular range, which is determined by a first predetermined value and second different predetermined value.

5. The apparatus of claim 4, wherein the control circuit is configured to control the said aspect of the processed electrical energy by controlling an amplitude and/or duty cycle or period of the processed electrical energy.

6. The apparatus of claim 1, wherein the electrical energy processing unit comprises a control circuit operable to control the converter to convert the unprocessed electrical energy to the processed electrical energy, wherein the converter comprises at least one sensor, the control circuit being operatively connected to the sensor to receive therefrom a converter feedback signal, the converter feedback signal comprising information to monitor an aspect of the processed electric energy, wherein the control circuit is configured to provide closed-loop control of the said aspect of the processed electrical energy using the said converter feedback signal.

7. The apparatus of claim 1, wherein the earth electrode comprises a substantially flat surface configured to receive the processed electrical energy when resting on a surface of the ground.

8. The apparatus of claim 1, wherein the applicator unit comprises a plurality of applicator electrodes.

9. The apparatus of claim 1, wherein the surface of the earth electrode that is configured to be placed substantially planar to the surface of the ground is not inserted into the ground.

10. A method of using an apparatus to electrically kill a plant or at least attenuate plant growth, comprising the steps of:
   obtaining an apparatus comprising an electrical energy processing unit, an applicator unit comprising an applicator electrode, and an earth unit comprising an earth electrode, wherein the electrical energy processing unit comprising a converter operable to receive unprocessed electrical energy from an electrical energy source, to convert the unprocessed electrical energy to processed electrical energy having an electrical current and to transmit the processed electrical energy between the applicator electrode of the applicator unit and the earth electrode of the earth unit, wherein each of the applicator unit and the earth unit is electrically coupled to the converter, and wherein each of the applicator electrode and the earth electrode comprises an electrically conductive material;
   directly contacting a portion of a plant that extends above the ground with the applicator electrode;
   disposing a surface of the earth electrode substantially planar to a surface of the ground so as to electrically couple the earth unit to the ground; and
   supplying processed electrical energy directly to the plant with the apparatus, wherein the processed electrical energy comprises a waveform with a frequency of at least 18 kHz and with a peak voltage of at least 1 kV and with an electrical current of at least 10 mA rms, wherein the applicator electrode directly transmits the processed electrical energy to the portion of the plant that extends above the ground such that the electrical current travels through the at least part of the plant above ground as part of a circuit and the electrical current returns to the earth electrode through the surface of the ground.

11. The method of claim 10, wherein the surface of the earth electrode is configured to receive the processed electrical energy when resting on a surface of the ground, and wherein the method further comprises the step of:
   moving the earth electrode of the earth unit along the surface of the ground whilst maintaining electrical continuity between the earth unit and the surface of the ground so as to electrically kill or at least attenuate growth of a first plant located at a first location and a second plant located at a second location.

12. The method of claim 10, wherein the surface of the earth electrode disposed substantially planar to a surface of the ground is not inserted into the ground.

13. An apparatus to electrically kill a plant or at least attenuate plant growth, the apparatus comprising:
   an electrical energy processing unit comprising a converter operable to receive unprocessed electrical energy from an electrical energy source, to convert the unprocessed electrical energy to processed electrical energy having an electrical current and to transmit the processed electrical energy between an applicator electrode of an applicator unit and an earth electrode of an earth unit,
   the applicator unit comprising the applicator electrode, wherein the applicator electrode comprises an electrically conductive material, the applicator unit being electrically coupled to the converter of the electrical energy processing unit wherein the applicator unit is operable to receive the processed electrical energy and to apply the processed electrical energy directly to at least a portion of a plant that extends above the ground; and
   the earth unit comprising the earth electrode, wherein the earth electrode comprises an electrically conductive material, the earth unit being electrically coupled to the converter, wherein the earth unit is operable to receive the processed electrical energy transmitted from the applicator unit through a load comprising the plant, and wherein the earth electrode comprises a surface that is configured to be placed substantially planar to a surface of the ground or inserted into the ground so as to electrically couple the earth unit to the ground; and
   wherein the applicator electrode is configured for direct transmission of the processed electrical energy to at least part of the plant above ground such that the electrical current travels through the at least part of the plant above ground as part of a circuit and the electrical current returns to the earth electrode through the ground, wherein the processed electrical energy comprises a waveform with a frequency of at least 18 kHz and with a peak voltage of at least 1 kV and with an electrical current of at least 10 mA rms.

14. The apparatus of claim 13, wherein the electrical energy processing unit is configured to produce processed electrical energy that comprises a power of at least 5 W.

15. The apparatus of claim 13, wherein the electrical energy processing unit is configured to produce processed electrical energy that is operable to kill a plant or at least partially attenuating plant growth with a treatment time of at least 10 milliseconds.

16. The apparatus of claim 13, wherein the electrical energy processing unit further comprises a control circuit operable to control the converter to convert the unprocessed electrical energy to the processed electrical energy, wherein the control circuit is configured to control an aspect of the processed electrical energy comprising one or a combination of the:
   voltage; current; power, the said aspect controlled to be:
      maintained substantially at a predetermined value; or
      below or above a predetermined value; or
      within a particular range, which is determined by a first predetermined value and second different predetermined value.

17. The apparatus of claim 16, wherein the control circuit is configured to control the said aspect of the processed electrical energy by controlling an amplitude and/or duty cycle or period of the processed electrical energy.

18. The apparatus of claim 13, wherein the electrical energy processing unit comprises a control circuit operable to control the converter to convert the unprocessed electrical energy to the processed electrical energy, wherein the converter comprises at least one sensor, the control circuit being operatively connected to the sensor to receive therefrom a converter feedback signal, the converter feedback signal comprising information to monitor an aspect of the processed electric energy, wherein the control circuit is configured to provide closed-loop control of the said aspect of the processed electrical energy using the said converter feedback signal.

19. The apparatus of claim 13, wherein the applicator unit comprises a plurality of applicator electrodes.

20. A method of using an apparatus to electrically kill a plant or at least attenuate plant growth, comprising the steps of:
   obtaining the apparatus of claim 13;

directly contacting a portion of a plant that extends above the ground with the applicator electrode;

disposing the surface of the earth electrode substantially planar to a surface of the ground or into the ground so as to electrically couple the earth unit to the ground; and supplying processed electrical energy directly to the plant with the apparatus, wherein the processed electrical energy comprises a waveform with a frequency of at least 18 kHz and with a peak voltage of at least 1 kV and with an electrical current of at least 10 mA rms, wherein the applicator electrode directly transmits the processed electrical energy to the portion of the plant that extends above the ground such that the electrical current travels through the at least part of the plant above ground as part of a circuit and the electrical current returns to the earth electrode through the surface of the ground.

* * * * *

UNITED STATES PATENT AND TRADEMARK OFFICE
CERTIFICATE OF CORRECTION

PATENT NO. : 11,083,185 B2
APPLICATION NO. : 16/803548
DATED : August 10, 2021
INVENTOR(S) : Diprose It is certified that error appears in the above-identified patent and that said Letters Patent is hereby corrected as shown below:

In the Claims

Column 28, Line 11-12: After "configured" delete "to be placed substantially planar to a surface of the ground".

Column 28, Line 20-21: After "electrode through the" delete "surface of the".

Column 28, Line 27: After "comprises a" delete "a".

Column 29, Line 26: After "surface of the ground" insert -- or into the ground --.

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*